US010857219B2

(12) United States Patent
Hildebrand et al.

(10) Patent No.: US 10,857,219 B2
(45) Date of Patent: Dec. 8, 2020

(54) COMPOSITIONS COMPRISING SOLUBLE HLA/M. TUBERCULOSIS-SPECIFIC LIGAND COMPLEXES AND METHODS OF PRODUCTION AND USE THEREOF

(71) Applicant: The Board of Regents of The University Of Oklahoma, Norman, OK (US)

(72) Inventors: William H. Hildebrand, Edmond, OK (US); Curtis McMurtrey, Oklahoma City, OK (US); David Lewinsohn, Portland, OR (US); Deborah Lewinsohn, Portland, OR (US); Melanie Harriff, Portland, OR (US)

(73) Assignees: The Board of Regents of the University of Oklahoma, Norman, OK (US); Oregon Health & Science University, Portland, OR (US); The United States Government as Represented by the Department of Veterans Affairs, Washington, DC (US)

( * ) Notice: Subject to any disclaimer, the term of this patent is extended or adjusted under 35 U.S.C. 154(b) by 1299 days.

(21) Appl. No.: 14/671,322

(22) Filed: Mar. 27, 2015

(65) Prior Publication Data
US 2015/0273039 A1    Oct. 1, 2015

Related U.S. Application Data

(60) Provisional application No. 61/972,202, filed on Mar. 28, 2014.

(51) Int. Cl.
*A61K 39/00* (2006.01)
*A61K 39/04* (2006.01)
*G01N 33/569* (2006.01)
*C07K 14/35* (2006.01)
*C07K 14/74* (2006.01)

(52) U.S. Cl.
CPC .............. *A61K 39/04* (2013.01); *C07K 14/35* (2013.01); *C07K 14/70539* (2013.01); *G01N 33/5695* (2013.01); *A61K 2039/605* (2013.01); *G01N 2469/10* (2013.01)

(58) Field of Classification Search
None
See application file for complete search history.

(56) References Cited

U.S. PATENT DOCUMENTS

| 4,683,202 | A | 7/1987 | Mullis |
| 5,256,541 | A | 10/1993 | Pouletty et al. |
| 5,270,169 | A | 12/1993 | Chang et al. |
| 5,292,641 | A | 3/1994 | Pouletty |
| 5,482,841 | A | 1/1996 | Buelow |
| 5,582,031 | A | 12/1996 | Rathbone |
| 5,710,248 | A | 1/1998 | Grose |
| 5,750,367 | A | 5/1998 | Chan |
| 5,776,746 | A | 7/1998 | Denney, Jr. |
| 5,798,209 | A | 8/1998 | Chan |
| 5,830,995 | A | 11/1998 | Shoyab et al. |
| 6,001,365 | A | 12/1999 | Peterson et al. |
| 6,232,445 | B1 | 5/2001 | Rhode et al. |
| 7,632,651 | B2 | 12/2009 | Boge et al. |
| 7,745,142 | B2 | 6/2010 | Boge et al. |
| 2003/0124613 | A1 | 7/2003 | Hildebrand et al. |
| 2003/0213004 | A1 | 11/2003 | Jakobovits et al. |
| 2005/0267020 | A1 | 12/2005 | Faure et al. |
| 2006/0034850 | A1 | 2/2006 | Weidanz et al. |
| 2007/0092530 | A1 | 4/2007 | Weidanz et al. |
| 2008/0207497 | A1 | 8/2008 | Ramakrishna et al. |

FOREIGN PATENT DOCUMENTS

| WO | 199317095 | 9/1993 |
| WO | 199511702 | 5/1995 |
| WO | 1997046256 | 12/1997 |
| WO | 199806749 | 2/1998 |
| WO | 2000023053 | 4/2000 |
| WO | 2002072627 | 9/2002 |
| WO | 2002083903 | 10/2002 |
| WO | 2002086122 | 10/2002 |
| WO | 2002094981 | 11/2002 |
| WO | 2011092253 A1 | 8/2011 |

OTHER PUBLICATIONS

Ravindranath et al (Molecular Immunology, 2011, 48: 423-430, available online Dec. 9, 2010) (Year: 2011).*
Miller et al (Journal of Immunol. 2003, 171: 1369-1375) (Year: 2003).*
Reinout et al ( J. Clin. Endocrinol. 2002, 87(2): 58-763) (Year: 2002).*
Coupel et al (Blood, 2007, 109(7): 2806-2814) (Year: 2007).*
Hernandez-Pando et al (Lancet, 2000, 356: 2133-2137) (Year: 2000).*
Kraemer et al (Stem Cells Int. 2015, article ID 346714, pp. 1-12) (Year: 2015).*
Zaer, et al.; "Antibody Screening by Enzyme-Linked Immunosorbent Assay Using Pooled Soluble HLA in Renal Transplant Candidates," Transplantation, (1997); vol. 63, No. 1, pp. 48-51.
Davenport, et al.; "HLA Class I Binding Moitifs Derived from Random Peptide Libraries Differ at the COOH Terminus From Those of Eluted Peptides," J. Exp. Med., (1997), vol. 185, No. 2, pp. 367-371.

(Continued)

*Primary Examiner* — G. R. Ewoldt
*Assistant Examiner* — Marianne DiBrino
(74) *Attorney, Agent, or Firm* — Knobbe Martens Olson & Bear LLP

(57) ABSTRACT

Compositions that include one isolated, class I HLA-E trimolecular complex that includes a peptide ligand unique to *M. tuberculosis*-infected cells are disclosed. Isolated compositions that include the three components of the trimolecular complex and/or a polynucleotide encoding one or more of the three components are also disclosed.

6 Claims, 1 Drawing Sheet
(1 of 1 Drawing Sheet(s) Filed in Color)

Specification includes a Sequence Listing.

(56) References Cited

OTHER PUBLICATIONS

Reich, et al.; "Stability of empty and peptide-loaded class II major histocompatibility complex molecules at neutral and endosomal pH: Comparison to class I proteins," Proc. Natl. Acad. Sci. USA, (1997), vol. 94, pp. 2495-2500.
De la Salle, et al.; "Human Peptide Transporter Deficiency—Importance of HLA-B in the Presentation of TAP-Independent EBV Antigens," J. Immunol., (1997), vol. 158, No. 10, pp. 4555-4563.
Tan, et al.; "A novel, highly efficient peptide-HLA class I binding assay using unfolded heavy chain molecules: identification of HIV-1 derived peptides that bind to HLA-A*0201 and HLA-A*0301," J. Immunol. Methods, (1997), vol. 205, No. 2, pp. 201-209.
Holland, et al.; "Synthetic peptides based on Chlamydia trachomatis antigens identify cytotoxic T lymphocyte responses in subjects from a trachoma-endemic population," Holland et al., Clin. Exp. Immunol., (1997), vol. 107, pp. 44-49.
Lone, et al. "In Vitro Induction of Specific Cytotoxic T Lymphocytes Using Recombinant Single-Chain MHC Class I/Peptide Complexes," Journal of Immunotherapy, (1998), vol. 21, No. 4, pp. 283-294.
Prilliman, et al.; "Complexity among constituents of the HLA-B*1501 peptide motif," Immunogenetics (1998), vol. 48, pp. 89-97.
Van Der Heeft, et al.; "A Microcapillary Column Switching HPLC-Electrspray Ionization MS System for the Direct Identification of Peptides Presented by Major Histocompatibility Complex Class I Molecules," Anal. Chem.,(1998), vol. 70, pp. 3742-3751.
Yoon, et al.; "Synthetic peptides of human papillomavirus type 18 E6 harboring HLA-A2.1 motiff can induce peptide-specific cytotoxic T-cells from peripheral blood mononuclear cells of healthy donors," Virus Research, (1998), vol. 54, pp. 23-29.
Brusic, et al. "MHCPEP, a database of MHC-binding peptides: update 1997," Nucleic Acids Research, (1998), vol. 26, No. 1, pp. 368-371.
Brusic, et al.; "Prediction of MHC class II-binding peptides using an evolutionary algorithm and articiial neural network," Bioinformatics (1998), vol. 14, No. 2, pp. 121-130.
Stevens, et al.; "Efficient Generation of Major Histocompatibility Complex Class I-Peptide Complexes Using Synthetic Peptide Libraries*," The Journal of Biological Chemistry, (1998), vol. 273, No. 5, pp. 2874-2884.
Honeyman, et al.; "Neural network-based prediction of candidate T-cell epitopes," Nat. Biotechnol., (1998), vol. 16, pp. 966-969.
Flad, et al.; "Direct Identification of Major Histocompatibility Complex Class I-bound Tumor-associated Peptide Antigens of a Renal Carcinoma Cell Line by a Novel Mass Spectrometric Method," Cancer Research, (1998), vol. 58, pp. 5803-5811.
Walter, et al.; "A mutant human β2-microglobulin can be used to generate diverse multimeric class I peptide complexes as specific probes for T cell receptors," Journal of Immunological Methods (1998), vol. 214, pp. 41-50.
Schafer, et al.; "Prediction of well-conserved HIV-1 ligands using a matrix-based algorithm, EpiMatrix," Vaccine, (1998), vol. 16, No. 19, pp. 1880-1884.
"Unisyn Strives for Flexibility and Scale," Membrane and Separation Technology News, (Mar. 1, 1998), ISSN 0737-8483.
Celia, et al.; "Structure and function of a memebrane-bound murine MHC class I molecule," Proc. Natl. Acad. Sci. USA, (1999), vol. 96, pp. 5634-5639.
Chang, et al.; "Identification of HLA-A3 and -B7-Restricted CTL Response to Hepatitis C Virus in Patients with Acute and Chronic Hepatitis C1," J. Immunol., (1999), vol. 162, pp. 1156-1164.
Prilliman, et al.; "HLA-B15 Peptide Ligands Are Preferentially Anchored at Their C Termini," J. Immunol., (1999), vol. 162, pp. 7277-7284.
Prilliman, et al.; "Alpha-2 domain polymorphism and HLA class I peptide loading," Tissue Antigens, (1999), vol. 54, pp. 450-460.
Rammensee, et al.; "SYFPEITHI: database for MHC ligands and peptide motifs," Immunogenetics, (1999), vol. 50, pp. 213-219.
Prilliman, et al.; "Peptide motif of the class I molecule HLA-B*1503," Immunogenetics, (1999), vol. 49, pp. 144-146.
Hollon, Tom "Clad Against All Clades—Can vaccinomics build a world HIV vaccine?," The Scientist, (2000), vol. 14, No. 18, pp. 1-2.
Human Immunology; "The American Society for HIstocompatibility and Immunogenetics 26th Annual Meeting Abstracts," (2000), vol. 61, Supplement 2.
Hickman, et al.; "C-Terminal Epitope Tagging Facilitates Comparative Ligand Mapping from MHC Class I Positive Cells," Human Immunology (2000), vol. 61, pp. 1339-1346.
Schönbach, et al.; "FIMM, a database of functional molecular immunology," Nucleic Acids Research, (2000), vol. 28, No. 1, pp. 222-224.
Schueler-Furman, et al; "Examination of possible structural constraints of MHC-binding peptides by assessment of their native structure within their source proteins," Proteins: Structure, Function, and Genetics, (2001), vol. 45, No. 1, pp. 47-54 (Only Abstract Provided).
Dédier, et al; "Use of fluorescence polarization to monitor MHC-peptide interations in solution," Journal of Immunological Methods, (2001), vol. 255, pp. 57-66.
Smith, et al.; "Lethality-based selection of recombinant genes in mammalian cells; Application to identifying tumor antigens," Nature Medicine, (2001), vol. 7, No. 8, pp. 967-972.
Berg, et al.; "A Novel DNA Methyltransferase I-Derived Peptide Eluted From Soluble HLA-A*0201 Induces Peptid-Specific, Tumor-Directed Cytotoxic T Cells," Int. J, Cancer, (2004), vol. 112, pp. 426-432.
Kageyama, et al.; "Effect of mutated transporters associated with antigen-processing 2 on characteristic major histocompatibility complex binding peptides: analysis using electrospray ionization tandem mass spectrometry," Rapid Commun. Mass Spectrom., (2004), vol. 18, pp. 995-1000.
Buchli, et al.; "Development and Validation of a Fluorescence Polarization-Based Competitive Peptide-Binding Assay for HLA-A*0201—A New Tool for Epitope Discovery," Biochemistry (2005), vol. 44, pp. 12491-12507.
Wittman, et al; "Antibody Targeting to a Class I MHC-Peptide Epitope Promotes Tumor Cell Death," J. Immunol., (2006), vol. 177, pp. 4187-4195.
Milner, et al.; "The Turnover Kinetics of Major Histocompatibility Complex Peptides of Human Cancer Cells*," Molecular and Cellular Proteomics, (2006); vol. 5, pp. 357-365.
Fuji, et al; "A Soluble Form of the HLA-G Antigen Is Encoded by a Messenger Ribonucleic Acid Containing Intron 4," J Immunol Methods, (1994), vol. 153, pp. 5516-5524.
Johnson, et al; "Rapid cloning of HLA class I cDNAs by locus specific PCR," J Immunol Methods, (2000), vol. 233, pp. 119-129.
Bainbridge, et al; "The short forms of HLA-G are unlikely to play a role in pregnancy because they are not expressed at the cell surface"; J Reprod Immunol, (2000), vol. 47, pp. 1-16.
Cereb, et al; "Induction of Microvariant-Specific CTL Lines Reactive to a Single Amino Acid Mismatch in Bulk Cultures Using a Transfectant Expressing a Single HLA Class I Molecule," J Immunol, vol. (1996), vol. 156, pp. 18-26.
Canadian Serial No. 2,438,376, William H. Hildebrand; Office Action, dated Mar. 12, 2012.
Lanciotti, et al.; Origin of the West Nile Virus Responsible for an Outbreak of Encephalitis in the Northeastern United States; Science (1999), vol. 286, pp. 2333-2337.
Van Els, et al.; "A single naturally processed measles virus peptide fully dominates the HLA-A*0201-associated peptide display and is mutated at its anchor position in persistent viral strains," Eur. J. Immunol. (2000), vol. 30, pp. 1172-1181.
Joosten, et al.; "*Mycobacterium tuberculosis* Peptides Presented by HLA-E Molecules Are Targets for Human CD8+ T-Cells with Cytotoxic as well as Regulatory Activity," PLoS Pathogens, (2010), vol. 6, No. 2, pp. 1-15.
Garces, et al.; "EspA Acts as a Critical Mediator of ESX1-Dependent Virulence in *Mycobacterium tuberculosis* by Affecting Bacterial Cell Wall Integrity," PLoS Pathogens, (2010), vol. 6, No. 6, pp. 1-11.

(56) References Cited

OTHER PUBLICATIONS

International Search Report, dated Sep. 4, 2015, in PCT/US2015/023058, filed Mar. 27, 2015.
Written Opinion of the International Searching Authority, dated Sep. 4, 2015, in PCT/US2015/023058, filed Mar. 27, 2015.
Maniatis, et al.; "Molecular Cloning A Laboratory Manual," Selected Text "RNA-Dependent DNA Polymerase—Isolation of mRNA from Mammalian Cells," Cold Spring Harbor Laboratory (1982), pp. 128-129 and 191-193.
Maniatis, et al.; "Molecular Cloning A Laboratory Manual," Selected Text "Synthesis and Cloning of cDNA," Cold Spring Harbor Laboratory (1982) vol. 1, pp. 213-245.
Plant, et al.; "Generic liposome reagent for immunoassays," Analytical Biochemistry, (1989) vol. 176, No. 2, pp. 420-426.
Townsend, et al.; "Assembly of MHC Class I Molecules Analyzed In Vitro," Cell (1990) vol. 62, pp. 285-295.
Falk, et al.; :Allele-specifric motifs revealed by sequencing of self-peptides eluted from MHC molecues, Nature (1991), vol. 351, pp. 290-296.
Hunt, et al; "Characterization of Peptides Bound to the Class I MHC Molecule HLA-A2.1 by Mass Spectrometry," Science (1992), vol. 255, pp. 1261-1263.
Matsumura, et al.; "In Vitro Peptide Binding to Soluble Empty Class I Major Histocompatibility Complex Molecules Isolated from Transfected *Drosophila melanogaster* Cells," The Journal of Biological Chemistry, (1992) vol. 267, No. 33, pp. 23589-23595.
Parker, et al.; "Peptide Binding to HLA-A2 and HLA-B27 Isolated from *Escherichia coli*," The Journal of Biological Chemistry (1992), vol. 267, No. 8, pp. 5451-5459.
Corr, et al.; "Endogenous Peptides of a Soluble Major Histocompatibiltiy Complex Class I Molecule, H-2Lds: Sequence Motif, Quantitative Binding, and Molecular Modeling of the Complex," The Journal of Experimental Medicine (1992), vol. 176, pp. 1681-1692.
Tanigaki, Nobuyuki; "The specificity and efficiency of endogenous peptides in the induction of HLA class I α chain refolding," Eur J. Immunol., (1992), vol. 22, pp. 2177-2180.
Calin-Laurens, et al.; "Can one predict antigenic peptides for MHC class I-restricted cytotoxic T lymphocytes useful for vaccination?," Vaccine (1993), vol. 11, No. 9, pp. 974-978.
Ojcius, et al.; "Dissociation of the Peptide-MHC Class I Complex Limits of the Binding Rate of Exogenous Peptide," Journal of Immunology (1993), vol. 151, No. 11, pp. 6020-6026.
Ojcius, et al.; "Dissociation of the Peptide/MHC Class I Complex: pH Dependence and Effect of Endogenous Peptides on the Activation Energy," Biochemical and Biophysical Research Communications (1993) vol. 197, No. 3, pp. 1216-1222.
Henderson, et al.; "Direct identification of an endogenous peptide recognized by multiple HLA-A2.1-specific cytotoxic T cells," Proc. Natl. Acad. Sci. USA (1993), vol. 90, pp. 10275-10279.
Huczko, et al.; "Characteristics of Endogenous Peptides Eluted from the Class I MHC Molecule HLA-B7 Determined by Mass Spectrometry and Computer Modeling," Journal of Immunology (1993), vol. 151, No. 5 pp. 2572-2587.
Dal Porto, et al.; "A soluble divalent class I major histocompatibility complex molecule inhibits alloreactive T cells at nanomolar concentrations," Proc. Natl. Acad. Sci. USA (1993), vol. 90, pp. 6671-6675.
Anton, et al; "The Accessibility of Peptides Bound to the Mouse MHC Class II Molecule IE-d Studied by Fluorescence", Federation of European Biochemical Societies Letters, (1994), vol. 342, No. 3, pp. 230-234; (Only Abstract provided).

Sette, et al.; "Peptide Binding to the Most Frequent HLA-A Class I Alleles Measured by Quantitative Molecular Binding Assays," Molecular Immunology (1994), vol. 31, No. 11, pp. 813-822.
Yang, et al.; "Targeted amplification of alternatively spliced transcripts of major histocompatibility complex class I heavy chain," Journal of Immunological Methods (1994), vol. 176, pp. 265-270.
Fisk, et al.; "Identifiation of an Immunodominant Peptide of HER-2/neu Protooncogene Recognized oby Ovarian Tumor-specific Cytotoxic T Lymphocyte Lines," Journal Exp. Med. (1995), vol. 181, pp. 2109-2117.
Del Guercio, et al.; "Binding of a Peptide Antigen to Multiple HLA Alleles Allows Definition of an A2-Like Suptertype," Journal of Immunology (1995), vol. 154, pp. 685-693.
Khilko, et al.; "Measuring interations of MHC class I molecules using surface plasmon resonance," J. Immunol. Methods (1995), vol. 183, pp. 77-94.
Falk et al.; "Peptide motifs of HLA-B58, B60, B61, and B62 molecules," Immunogenetics (1995), vol. 41, pp. 165-168.
Davenport, et al.; "An empirical method for the prediction of T-cell epitopes," Immunogenetics, (1995), vol. 42, pp. 392-397.
Falk, et al; "Peptide Motifs of HLA-B38 and B39 Molecules," Immunogenetics, (1995), vol. 41, pp. 162-164.
Drijfhout, et al.; "Detailed Motifs for Peptide Binding to HLA*0201 Derived from Large Random Sets of Peptides Using a Cellular Binding Assay." Human Immunology (1995) vol. 43, pp. 1-12.
Appella, et al.; "Analysis of the Structure of Naturally Processed Peptides Bound by Class I and Class II Major Histocompatibility Complex Molecules," Exs., (1995), vol. 73, pp. 105-119. (Only Abstract Provided).
Gnjatic, et al; "Mapping and Ranking of Potential Cytotoxic T Epitopes in the p53 Protein: Effect of Mutations and Polymorphism on Peptide Binding to Purified and Refolded HLA Molecules," Eur. J. Immunol., (1995), vol. 25, pp. 1638-1642.
Woods, et al.; "Simplified High-Sensitivity Sequencing of a Major Histocompatibilty Complex Class I-Associated Immunoreative Peptide Using Matrix-Assisted Laser Desorption/Ionization Mass Spectrometry," Analytical Biochemistry (1995), vol. 226, pp. 15-25.
Smith, et al.; "Probing HLA-B7 Conformational Shifts Induced by Peptide-Binding Groove Mutations and Bound Peptide with Anti-HLA Monoclonal Antibodies," The Journal of Immunolgoy, (1996), vol. 157, pp. 2470-2478.
Mizuno, et al; "A new murine lymphocytotoxic monoclonal antibody recognizing HLA-A2, -A28 and -A9," Tissue Antigens, (1996), vol. 48, pp. 224-227.
Sumitran-Karuppan, et al; "The Use of Magnetic Beads Coated With Soluble HLA Class I or Class II Proteins in Antibody Screening and for Specificity Determination of Donor-Reactive Antibodies," Transplantation (1996), vol. 61, No. 10, pp. 1539-1545.
Gulukota, et al.; "HLA allele selection for designing peptide vaccines," Genetic Analysis: Biomolecular Engineering, (1996), vol. 13, pp. 81-86.
Jackson, et al.; "Evaluation of hollow fiber bioreactors as an alternative to murine ascites production for small scale monoclonal antibody production," J. Immunol. Methods, (1996), vol. 189, pp. 217-231.
Walden, Peter; "T-Cell epitope determination," Curr Opin Immunol., (1996), vol. 8, pp. 68-74.
Prillman, et al.; "Large-scale produciton of class I bound peptides: assigning a signature to HLA-B*1501," Immunogentics, (1997), vol. 45, pp. 379-385.

\* cited by examiner

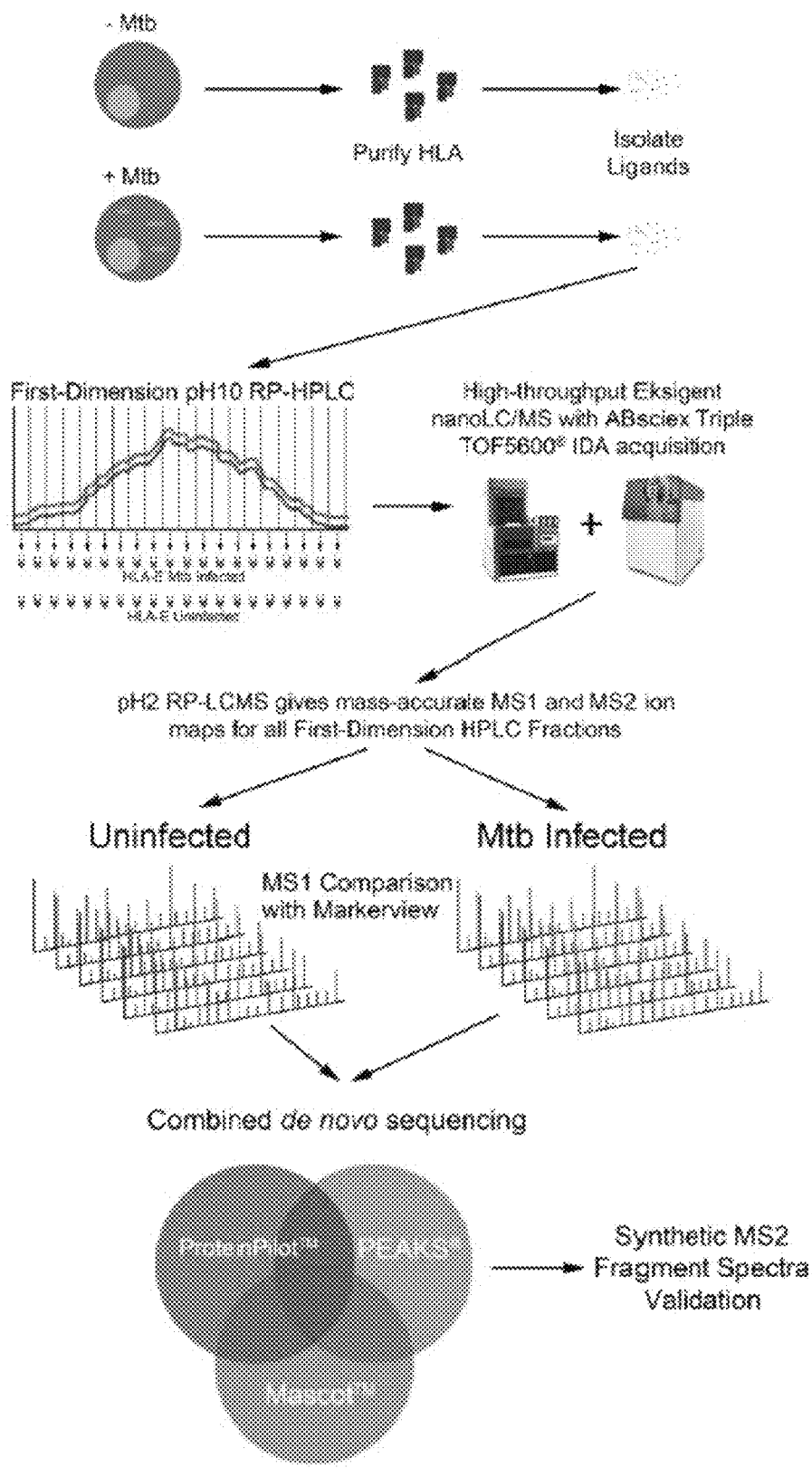

SEQUENCE LISTING

<160> NUMBER OF SEQ ID NOS: 44

<210> SEQ ID NO 1
<211> LENGTH: 20
<212> TYPE: PRT
<213> ORGANISM: Mycobacterium tuberculosis

```
<400> SEQUENCE: 1

Ala Glu Arg Ala Pro Val Glu Ala Asp Ala Gly Gly Gly Gln Lys Val
1               5                   10                  15

Leu Val Arg Asn
            20

<210> SEQ ID NO 2
<211> LENGTH: 11
<212> TYPE: PRT
<213> ORGANISM: Mycobacterium tuberculosis

<400> SEQUENCE: 2

Ser Thr Glu Gly Asn Val Thr Gly Met Phe Ala
1               5                   10

<210> SEQ ID NO 3
<211> LENGTH: 11
<212> TYPE: PRT
<213> ORGANISM: Mycobacterium tuberculosis
<220> FEATURE:
<221> NAME/KEY: MISC_FEATURE
<222> LOCATION: (9)..(9)
<223> OTHER INFORMATION: oxidized methionine

<400> SEQUENCE: 3

Ser Thr Glu Gly Asn Val Thr Gly Met Phe Ala
1               5                   10

<210> SEQ ID NO 4
<211> LENGTH: 9
<212> TYPE: PRT
<213> ORGANISM: Mycobacterium tuberculosis

<400> SEQUENCE: 4

Leu Leu Asp Glu Gly Lys Gln Ser Leu
1               5

<210> SEQ ID NO 5
<211> LENGTH: 10
<212> TYPE: PRT
<213> ORGANISM: Mycobacterium tuberculosis

<400> SEQUENCE: 5

Ser Leu Leu Asp Glu Gly Lys Gln Ser Leu
1               5                   10

<210> SEQ ID NO 6
<211> LENGTH: 9
<212> TYPE: PRT
<213> ORGANISM: Mycobacterium tuberculosis

<400> SEQUENCE: 6

Ser Leu Leu Asp Ala His Ile Pro Gln
1               5

<210> SEQ ID NO 7
<211> LENGTH: 10
<212> TYPE: PRT
<213> ORGANISM: Mycobacterium tuberculosis

<400> SEQUENCE: 7

Ser Leu Leu Asp Ala His Ile Pro Gln Leu
1               5                   10
```

```
<210> SEQ ID NO 8
<211> LENGTH: 9
<212> TYPE: PRT
<213> ORGANISM: Mycobacterium tuberculosis

<400> SEQUENCE: 8

Leu Leu Asp Ala His Ile Pro Gln Leu
1               5

<210> SEQ ID NO 9
<211> LENGTH: 8
<212> TYPE: PRT
<213> ORGANISM: Mycobacterium tuberculosis

<400> SEQUENCE: 9

Leu Leu Asp Ala His Ile Pro Gln
1               5

<210> SEQ ID NO 10
<211> LENGTH: 18
<212> TYPE: PRT
<213> ORGANISM: Mycobacterium tuberculosis

<400> SEQUENCE: 10

Thr Leu Leu Asp Val Ala Gln Ala Asn Leu Gly Glu Ala Ala Gly Thr
1               5                   10                  15

Tyr Val

<210> SEQ ID NO 11
<211> LENGTH: 10
<212> TYPE: PRT
<213> ORGANISM: Mycobacterium tuberculosis

<400> SEQUENCE: 11

Asn Leu Gly Glu Ala Ala Gly Thr Tyr Val
1               5                   10

<210> SEQ ID NO 12
<211> LENGTH: 9
<212> TYPE: PRT
<213> ORGANISM: Mycobacterium tuberculosis

<400> SEQUENCE: 12

Ile Met Tyr Asn Tyr Pro Ala Met Leu
1               5

<210> SEQ ID NO 13
<211> LENGTH: 9
<212> TYPE: PRT
<213> ORGANISM: Mycobacterium tuberculosis
<220> FEATURE:
<221> NAME/KEY: MISC_FEATURE
<222> LOCATION: (2)..(2)
<223> OTHER INFORMATION: oxidized methionine
<220> FEATURE:
<221> NAME/KEY: MISC_FEATURE
<222> LOCATION: (8)..(8)
<223> OTHER INFORMATION: oxidized methionine

<400> SEQUENCE: 13

Ile Met Tyr Asn Tyr Pro Ala Met Leu
1               5
```

```
<210> SEQ ID NO 14
<211> LENGTH: 10
<212> TYPE: PRT
<213> ORGANISM: Mycobacterium tuberculosis

<400> SEQUENCE: 14

Pro Ala Leu Pro Pro Ala Pro Pro Ser Pro
1               5                   10

<210> SEQ ID NO 15
<211> LENGTH: 10
<212> TYPE: PRT
<213> ORGANISM: Mycobacterium tuberculosis

<400> SEQUENCE: 15

Leu Pro Pro Ala Pro Pro Ala Pro Pro Ser
1               5                   10

<210> SEQ ID NO 16
<211> LENGTH: 15
<212> TYPE: PRT
<213> ORGANISM: Mycobacterium tuberculosis

<400> SEQUENCE: 16

Gly Leu Ile Asp Ile Ala Pro His Gln Ile Ser Ser Val Ala Ala
1               5                   10                  15

<210> SEQ ID NO 17
<211> LENGTH: 12
<212> TYPE: PRT
<213> ORGANISM: Mycobacterium tuberculosis

<400> SEQUENCE: 17

Gly Gly Ile Leu Ile Gly Ser Asp Thr Asp Leu Thr
1               5                   10

<210> SEQ ID NO 18
<211> LENGTH: 14
<212> TYPE: PRT
<213> ORGANISM: Mycobacterium tuberculosis

<400> SEQUENCE: 18

His Val Gly Gly Ile Leu Ile Gly Ser Asp Thr Asp Leu Thr
1               5                   10

<210> SEQ ID NO 19
<211> LENGTH: 13
<212> TYPE: PRT
<213> ORGANISM: Mycobacterium tuberculosis

<400> SEQUENCE: 19

Val Gly Gly Ile Leu Ile Gly Ser Asp Thr Asp Leu Thr
1               5                   10

<210> SEQ ID NO 20
<211> LENGTH: 12
<212> TYPE: PRT
<213> ORGANISM: Mycobacterium tuberculosis

<400> SEQUENCE: 20

Ala Glu Ile Val Ala Gly Gly Gly Pro Leu Pro Leu
1               5                   10
```

-continued

```
<210> SEQ ID NO 21
<211> LENGTH: 10
<212> TYPE: PRT
<213> ORGANISM: Mycobacterium tuberculosis

<400> SEQUENCE: 21

Pro Ala Ile Leu Arg Pro Gly Arg Leu Asp
1               5                   10

<210> SEQ ID NO 22
<211> LENGTH: 10
<212> TYPE: PRT
<213> ORGANISM: Mycobacterium tuberculosis

<400> SEQUENCE: 22

Arg Val Val Pro Glu Gly Leu Ala Ala Ala
1               5                   10

<210> SEQ ID NO 23
<211> LENGTH: 11
<212> TYPE: PRT
<213> ORGANISM: Mycobacterium tuberculosis

<400> SEQUENCE: 23

Ala Asp Val Val Gly Ser Asp Asp Leu Ile Glu
1               5                   10

<210> SEQ ID NO 24
<211> LENGTH: 13
<212> TYPE: PRT
<213> ORGANISM: Mycobacterium tuberculosis

<400> SEQUENCE: 24

Ala Gly Ala Asp Val Val Gly Ser Asp Asp Leu Ile Glu
1               5                   10

<210> SEQ ID NO 25
<211> LENGTH: 9
<212> TYPE: PRT
<213> ORGANISM: Mycobacterium tuberculosis

<400> SEQUENCE: 25

Ala Thr Asn Arg Pro Asp Leu Ile Asp
1               5

<210> SEQ ID NO 26
<211> LENGTH: 8
<212> TYPE: PRT
<213> ORGANISM: Mycobacterium tuberculosis

<400> SEQUENCE: 26

Thr Asn Arg Pro Asp Leu Ile Asp
1               5

<210> SEQ ID NO 27
<211> LENGTH: 11
<212> TYPE: PRT
<213> ORGANISM: Mycobacterium tuberculosis

<400> SEQUENCE: 27

Glu Ile Glu Val Asp Asp Asp Leu Ile Gln Lys
1               5                   10
```

-continued

```
<210> SEQ ID NO 28
<211> LENGTH: 12
<212> TYPE: PRT
<213> ORGANISM: Mycobacterium tuberculosis
<220> FEATURE:
<221> NAME/KEY: MISC_FEATURE
<222> LOCATION: (1)..(1)
<223> OTHER INFORMATION: N-terminal acetylation

<400> SEQUENCE: 28

Ser Thr Ile Ile Ala Gly Ala Leu Leu Leu Val Leu
1               5                   10

<210> SEQ ID NO 29
<211> LENGTH: 8
<212> TYPE: PRT
<213> ORGANISM: Mycobacterium tuberculosis

<400> SEQUENCE: 29

Leu Ile Gly Pro Pro Pro Ser Pro
1               5

<210> SEQ ID NO 30
<211> LENGTH: 392
<212> TYPE: PRT
<213> ORGANISM: Mycobacterium tuberculosis

<400> SEQUENCE: 30

Met Ser Arg Ala Phe Ile Ile Asp Pro Thr Ile Ser Ala Ile Asp Gly
1               5                   10                  15

Leu Tyr Asp Leu Leu Gly Ile Gly Ile Pro Asn Gln Gly Gly Ile Leu
                20                  25                  30

Tyr Ser Ser Leu Glu Tyr Phe Glu Lys Ala Leu Glu Leu Ala Ala
            35                  40                  45

Ala Phe Pro Gly Asp Gly Trp Leu Gly Ser Ala Ala Asp Lys Tyr Ala
    50                  55                  60

Gly Lys Asn Arg Asn His Val Asn Phe Phe Gln Glu Leu Ala Asp Leu
65                  70                  75                  80

Asp Arg Gln Leu Ile Ser Leu Ile His Asp Gln Ala Asn Ala Val Gln
                85                  90                  95

Thr Thr Arg Asp Ile Leu Glu Gly Ala Lys Lys Gly Leu Glu Phe Val
            100                 105                 110

Arg Pro Val Ala Val Asp Leu Thr Tyr Ile Pro Val Val Gly His Ala
        115                 120                 125

Leu Ser Ala Ala Phe Gln Ala Pro Phe Cys Ala Gly Ala Met Ala Val
    130                 135                 140

Val Gly Gly Ala Leu Ala Tyr Leu Val Val Lys Thr Leu Ile Asn Ala
145                 150                 155                 160

Thr Gln Leu Leu Lys Leu Leu Ala Lys Leu Ala Glu Leu Val Ala Ala
                165                 170                 175

Ala Ile Ala Asp Ile Ile Ser Asp Val Ala Asp Ile Ile Lys Gly Thr
            180                 185                 190

Leu Gly Glu Val Trp Glu Phe Ile Thr Asn Ala Leu Asn Gly Leu Lys
        195                 200                 205

Glu Leu Trp Asp Lys Leu Thr Gly Trp Val Thr Gly Leu Phe Ser Arg
    210                 215                 220

Gly Trp Ser Asn Leu Glu Ser Phe Phe Ala Gly Val Pro Gly Leu Thr
225                 230                 235                 240
```

```
Gly Ala Thr Ser Gly Leu Ser Gln Val Thr Gly Leu Phe Gly Ala Ala
            245                 250                 255

Gly Leu Ser Ala Ser Ser Gly Leu Ala His Ala Asp Ser Leu Ala Ser
        260                 265                 270

Ser Ala Ser Leu Pro Ala Leu Ala Gly Ile Gly Gly Ser Gly Phe
    275                 280                 285

Gly Gly Leu Pro Ser Leu Ala Gln Val His Ala Ala Ser Thr Arg Gln
        290                 295                 300

Ala Leu Arg Pro Arg Ala Asp Gly Pro Val Ala Ala Ala Glu Gln
305                 310                 315                 320

Val Gly Gly Gln Ser Gln Leu Val Ser Ala Gln Gly Ser Gln Gly Met
            325                 330                 335

Gly Gly Pro Val Gly Met Gly Gly Met His Pro Ser Ser Gly Ala Ser
            340                 345                 350

Lys Gly Thr Thr Thr Lys Lys Tyr Ser Glu Gly Ala Ala Ala Gly Thr
            355                 360                 365

Glu Asp Ala Glu Arg Ala Pro Val Glu Ala Asp Ala Gly Gly Gly Gln
    370                 375                 380

Lys Val Leu Val Arg Asn Val Val
385                 390

<210> SEQ ID NO 31
<211> LENGTH: 95
<212> TYPE: PRT
<213> ORGANISM: Mycobacterium tuberculosis

<400> SEQUENCE: 31

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
                20                  25                  30

Lys Gln Ser Leu Thr Lys Leu Ala Ala Ala Trp Gly Gly Ser Gly Ser
            35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 32
<211> LENGTH: 97
<212> TYPE: PRT
<213> ORGANISM: Mycobacterium tuberculosis

<400> SEQUENCE: 32

Met Ser Leu Leu Asp Ala His Ile Pro Gln Leu Val Ala Ser Gln Ser
1               5                   10                  15

Ala Phe Ala Ala Lys Ala Gly Leu Met Arg His Thr Ile Gly Gln Ala
                20                  25                  30

Glu Gln Ala Ala Met Ser Ala Gln Ala Phe His Gln Gly Glu Ser Ser
            35                  40                  45

Ala Ala Phe Gln Ala Ala His Ala Arg Phe Val Ala Ala Ala Lys
    50                  55                  60

Val Asn Thr Leu Leu Asp Val Ala Gln Ala Asn Leu Gly Glu Ala Ala
65                  70                  75                  80
```

```
Gly Thr Tyr Val Ala Ala Asp Ala Ala Ala Ala Ser Thr Tyr Thr Gly
                85                  90                  95

Phe

<210> SEQ ID NO 33
<211> LENGTH: 96
<212> TYPE: PRT
<213> ORGANISM: Mycobacterium tuberculosis

<400> SEQUENCE: 33

Met Ser Gln Ile Met Tyr Asn Tyr Pro Ala Met Leu Gly His Ala Gly
1               5                   10                  15

Asp Met Ala Gly Tyr Ala Gly Thr Leu Gln Ser Leu Gly Ala Glu Ile
            20                  25                  30

Ala Val Glu Gln Ala Ala Leu Gln Ser Ala Trp Gln Gly Asp Thr Gly
        35                  40                  45

Ile Thr Tyr Gln Ala Trp Gln Ala Gln Trp Asn Gln Ala Met Glu Asp
    50                  55                  60

Leu Val Arg Ala Tyr His Ala Met Ser Ser Thr His Glu Ala Asn Thr
65                  70                  75                  80

Met Ala Met Met Ala Arg Asp Thr Ala Glu Ala Ala Lys Trp Gly Gly
                85                  90                  95

<210> SEQ ID NO 34
<211> LENGTH: 763
<212> TYPE: PRT
<213> ORGANISM: Mycobacterium tuberculosis

<400> SEQUENCE: 34

Met Pro Pro Val Pro Ala Pro Arg Ala Leu Ala Pro Leu Pro Pro Ala
1               5                   10                  15

Pro Pro Ala Pro Ala Glu Pro Lys Ser Lys Pro Pro Phe Pro Pro Ala
            20                  25                  30

Pro Pro Ala Pro Pro Cys Trp Met Leu Val Ser Ala Ala Pro Pro Cys
        35                  40                  45

Pro Pro Ala Pro Pro Ala Pro Pro Lys Pro Lys Ser Lys Ala Pro Phe
    50                  55                  60

Pro Pro Val Pro Pro Ala Pro Pro Ala Arg Glu Leu Ala Pro Pro Leu
65                  70                  75                  80

Pro Pro Ala Pro Pro Glu Ala Pro Arg Glu Ser Arg Pro Ala Leu Pro
                85                  90                  95

Pro Cys Pro Pro Pro Pro Val Val Ile Pro Asp Pro Pro Glu Pro Ala
            100                 105                 110

Ala Pro Pro Val Pro Pro Ala Pro Asn Ser Pro Pro Phe Pro Pro Phe
        115                 120                 125

Pro Pro Ala Pro Lys Phe Val Pro Ala Pro Pro Val Pro Pro Val Pro
    130                 135                 140

Asn Ser Pro Pro Phe Pro Pro Phe Pro Pro Ala Ala Leu Asn Pro Pro
145                 150                 155                 160

Ala Pro Pro Ala Pro Pro Leu Ala Asn Ser Pro Pro Leu Pro Pro Ala
                165                 170                 175

Pro Pro Thr Pro Ala Gly Thr Pro Pro Ala Ala Pro Trp Pro Pro Val
            180                 185                 190

Pro Ala Ala Pro Lys Ser Lys Pro Ala Ser Pro Pro Arg Pro Pro Ala
        195                 200                 205
```

```
Pro Pro Met Pro Ala Thr Pro Met Glu Phe Pro Pro Leu Pro Pro Val
    210                 215                 220
Pro Pro Asp Pro Ile Ser Lys Glu Thr Pro Pro Ala Pro Pro Ala Pro
225                 230                 235                 240
Pro Ile Pro Pro Ala Pro Val Pro Ile Pro Pro Val Pro Pro Leu Pro
                245                 250                 255
Pro Val Pro Asn Lys Ile Pro Pro Ala Pro Pro Ala Pro Pro Val Ala
            260                 265                 270
Val Ala Ala Val Leu Val Ala Pro Cys Pro Pro Leu Pro Pro Leu Pro
        275                 280                 285
Asn Asn His Pro Pro Ala Pro Pro Ala Ala Pro Val Pro Gly Val Pro
    290                 295                 300
Leu Ala Pro Leu Pro Asn Ser His Pro Pro Ala Pro Pro Ser Ala Pro
305                 310                 315                 320
Val Pro Gly Val Pro Leu Ala Pro Leu Pro Ile Ser Gly Arg Pro Val
                325                 330                 335
Ser Val Trp Lys Gly Ser Phe Thr Thr Leu Ser Thr Phe Cys Cys Arg
            340                 345                 350
Val Cys Ser Gly Glu Val Leu Ala Gly Ala Leu Asn Pro Ser Arg Pro
        355                 360                 365
Ser Arg Ser Pro Leu Thr Thr Thr Pro Ala Leu Pro Ala Pro Ile
    370                 375                 380
Pro Pro Leu Pro Pro Leu Pro Pro Leu Pro Ile Asn Thr Ala Val Pro
385                 390                 395                 400
Pro Ile Pro Pro Leu Pro Pro Val Thr Ala Leu Ala Pro Pro Leu Pro
                405                 410                 415
Pro Leu Ala Pro Leu Pro Ile Ser Pro Gly Val Pro Pro Ala Pro Pro
            420                 425                 430
Ile Pro Pro Gly Lys Pro Trp Thr Thr Pro Pro Leu Ala Pro Ala Pro
        435                 440                 445
Pro Glu Pro Lys Thr Val Pro Val Leu Pro Pro Gly Pro Ser Cys Pro
    450                 455                 460
Pro Ser Glu Lys Pro Asn Pro Pro Ala Pro Pro Glu Pro Pro Glu Pro
465                 470                 475                 480
Lys Ser Ser Pro Ala Leu Pro Pro Ala Pro Pro Ala Pro Ser Met Pro
                485                 490                 495
Ser Ala Val Arg Val Pro Pro Ser Pro Pro Ile Pro Pro Ala Pro Pro
            500                 505                 510
Ala Ala Pro Arg Ala Ser Met Pro Ala Leu Pro Pro Ala Pro Pro Ser
        515                 520                 525
Pro Pro Ala Thr Arg Leu Cys Pro Pro Leu Pro Pro Ser Pro Pro Ala
    530                 535                 540
Pro Asn Ser Pro Pro Ala Pro Pro Ala Pro Pro Thr Pro Pro Lys Leu
545                 550                 555                 560
Leu Ser Ala Asn Pro Pro Cys Pro Pro Val Pro Pro Ala Pro Asn Arg
                565                 570                 575
Pro Pro Ala Pro Pro Ala Pro Pro Ala Pro Pro Glu Leu Pro Ala Pro
            580                 585                 590
Pro Asp Pro Pro Thr Pro Pro Val Ala Asn Ser Pro Pro Ala Pro Pro
        595                 600                 605
Ala Pro Pro Ala Pro Pro Ser Ala Leu Pro Phe Val Asn Pro Pro Ala
610                 615                 620
```

```
Pro Pro Thr Pro Ala Ala Pro Lys Ser Arg Pro Ala Leu Pro Ala Ala
625                 630                 635                 640

Pro Pro Ala Pro Ala Pro Pro Val Arg Ala Thr Thr Pro Pro Pro
            645                 650                 655

Ala Pro Pro Ala Pro Pro Ala Pro Asn Ser Met Ala Leu Pro Pro Ala
                660                 665                 670

Pro Pro Asp Pro Pro Ile Pro Leu Leu Ala Thr Pro Pro Ala Pro Pro
            675                 680                 685

Ala Pro Pro Leu Pro Met Ser Pro Pro Ala Pro Pro Leu Pro Pro Ala
            690                 695                 700

Ala Pro Asp Pro Pro Ala Pro Pro Leu Thr Ile Asn Gln Pro Pro Ser
705                 710                 715                 720

Pro Pro Leu Ala Pro Val Pro Gly Ala Pro Leu Ala Pro Leu Pro Ile
            725                 730                 735

Asn Gly Arg Pro Val Phe Ala Arg Lys Asn Ser Leu Ile Gly Ser Ser
            740                 745                 750

Ser Gly Asp Thr Ala Ala Ala Ser Ala Ala Ala
            755                 760

<210> SEQ ID NO 35
<211> LENGTH: 479
<212> TYPE: PRT
<213> ORGANISM: Mycobacterium tuberculosis

<400> SEQUENCE: 35

Met Pro Pro Ser Thr Val Leu Ala Pro Ile Pro Pro Ala Pro Pro
1               5                   10                  15

Ser Pro Ser Ser Gln Pro Pro Ala Pro Pro Ala Pro Pro Ala Pro Pro
            20                  25                  30

Pro Pro Ala Glu Leu Pro Pro Ala Pro Pro Ala Pro Val Pro His
            35                  40                  45

Ser Pro Ala Ala Pro Pro Ala Pro Pro Gly Ala Pro Glu Pro Ala Ala
            50                  55                  60

Pro Asp Pro Pro Ala Pro Pro Ser Pro Ser Ser His Pro Pro Gly Ala
65                  70                  75                  80

Pro Val Ala Pro Leu Pro Thr Ala Pro Gly Val Pro Leu Pro Ile Ser
            85                  90                  95

Gly Arg Pro Val Ser Val Trp Val Gly Ala Leu Ile Ala Ala Ser Ala
            100                 105                 110

Cys Cys Phe Arg Val Cys Ser Gly Glu Ala Leu Ala Gly Ala Leu Lys
            115                 120                 125

Pro Ser Ala Pro Ser Ser Ser Pro Leu Ile Pro Pro Ala Pro Val Ser
            130                 135                 140

Pro Ala Val Gly Pro Val Pro Pro Met Pro Ala Leu Pro Pro Leu Pro
145                 150                 155                 160

Ile Ser Thr Pro Ser Pro Pro Ala Pro Pro Val Pro Pro Val Thr Ala
            165                 170                 175

Pro Cys Pro Pro Ala Pro Pro Ala Pro Pro Leu Pro Ile Ser Asn Pro
            180                 185                 190

Ala Leu Pro Pro Ala Pro Pro Thr Pro Pro Ser Pro Val Ser Pro Asn
            195                 200                 205

Pro Pro Ala Pro Pro Thr Pro Pro Glu Pro Asn Gln Pro Ala Ser Pro
            210                 215                 220

Pro Ala Pro Pro Ala Pro Pro Ser Val Ser Pro Asn Pro Pro Val Pro
225                 230                 235                 240
```

```
Pro Asp Pro Ala Leu Pro Asn Ser Thr Pro Ala Leu Pro Pro Ala Pro
                    245                 250                 255

Pro Ala Pro Pro Ser Pro Arg Pro Ala Pro Asp Pro Pro Val
            260                 265                 270

Pro Pro Ala Pro Asn Ser Ser Pro Ala Leu Pro Pro Ala Pro Pro Thr
        275                 280                 285

Pro Pro Ser Leu Arg Lys Pro Arg Pro Val Pro Pro Ala Pro Pro
        290                 295                 300

Gly Pro Ala Ser Ser Pro Ala Pro Pro Ala Pro Thr Pro Pro
305                 310                 315                 320

Val Thr Ala Pro Ser Pro Pro Ala Pro Pro Cys Pro Pro Ala Pro Asn
                325                 330                 335

Ser Pro Pro Ala Pro Pro Thr Pro Pro Ala Pro Pro Ala Pro Ala Pro
                340                 345                 350

Ser Pro Pro Thr Pro Pro Thr Pro Pro Val Pro Asn Asn Gln Pro Pro
                355                 360                 365

Asp Pro Pro Ala Pro Pro Ala Pro Pro Ser Pro Thr Val Glu Leu Pro
        370                 375                 380

Pro Ala Pro Pro Ala Pro Pro Val Pro Asn Asn Pro Ala Ala Pro Pro
385                 390                 395                 400

Ala Pro Pro Gly Arg Pro Glu Pro Ala Ala Asp Pro Pro Ala Pro
                405                 410                 415

Pro Leu Pro Ser Asn His Pro Pro Gly Ala Pro Leu Ala Pro Val Pro
                420                 425                 430

Gly Ala Pro Leu Ala Pro Leu Pro Ile Asn Gly Arg Pro Val Ser Ala
                435                 440                 445

Thr Leu Cys Ala Leu Thr Ala Ala Ser Arg Ser Cys Cys Thr Leu Cys
450                 455                 460

Ala Gly Leu Ala Ser Thr Ala Ala Pro Ala Ala Ser Ala Leu Ala
465                 470                 475

<210> SEQ ID NO 36
<211> LENGTH: 479
<212> TYPE: PRT
<213> ORGANISM: Mycobacterium tuberculosis

<400> SEQUENCE: 36

Met Thr Ser Leu Ile Asp Tyr Ile Leu Ser Leu Phe Arg Ser Glu Asp
1               5                   10                  15

Ala Ala Arg Ser Phe Val Ala Ala Pro Gly Arg Ala Met Thr Ser Ala
                20                  25                  30

Gly Leu Ile Asp Ile Ala Pro His Gln Ile Ser Ser Val Ala Ala Asn
            35                  40                  45

Val Val Pro Gly Leu Asn Leu Gly Ala Gly Asp Pro Met Ser Gly Leu
        50                  55                  60

Arg Gln Ala Val Ala Ala Arg His Gly Phe Ala Gln Asp Val Ala Asn
65                  70                  75                  80

Val Gly Phe Ala Gly Asp Ala Gly Ala Gly Val Ala Ser Val Ile Thr
                85                  90                  95

Thr Asp Val Gly Ala Gly Leu Ala Ser Gly Leu Gly Ala Gly Phe Leu
            100                 105                 110

Gly Gln Gly Gly Leu Ala Leu Ala Ala Ser Ser Gly Gly Phe Gly Gly
        115                 120                 125

Gln Val Gly Leu Ala Ala Gln Val Gly Leu Gly Phe Thr Ala Val Ile
    130                 135                 140
```

Glu Ala Glu Val Gly Ala Gln Val Gly Ala Gly Leu Gly Ile Gly Thr
145                 150                 155                 160

Gly Leu Gly Ala Gln Ala Gly Met Gly Phe Gly Gly Gly Val Gly Leu
            165                 170                 175

Gly Leu Gly Gly Gln Ala Gly Gly Val Ile Gly Gly Ser Ala Ala Gly
            180                 185                 190

Ala Ile Gly Ala Gly Val Gly Gly Arg Leu Gly Gly Asn Gly Gln Ile
        195                 200                 205

Gly Val Ala Gly Gln Gly Ala Val Gly Ala Gly Gly Ala Gly Val
    210                 215                 220

Gly Gly Gln Ala Gly Ile Ala Ser Gln Ile Gly Val Ser Ala Gly Gly
225                 230                 235                 240

Gly Leu Gly Gly Val Gly Asn Val Ser Gly Leu Thr Gly Val Ser Ser
            245                 250                 255

Asn Ala Val Leu Ala Ser Asn Ala Ser Gly Gln Ala Gly Leu Ile Ala
            260                 265                 270

Ser Glu Gly Ala Ala Leu Asn Gly Ala Ala Met Pro His Leu Ser Gly
    275                 280                 285

Pro Leu Ala Gly Val Gly Val Gly Gly Gln Ala Gly Ala Ala Gly Gly
    290                 295                 300

Ala Gly Leu Gly Phe Gly Ala Val Gly His Pro Thr Pro Gln Pro Ala
305                 310                 315                 320

Ala Leu Gly Ala Ala Gly Val Val Ala Lys Thr Glu Ala Ala Gly
            325                 330                 335

Val Val Gly Gly Val Gly Gly Ala Thr Ala Ala Gly Val Gly Gly Ala
            340                 345                 350

His Gly Asp Ile Leu Gly His Glu Gly Ala Ala Leu Gly Ser Val Asp
        355                 360                 365

Thr Val Asn Ala Gly Val Thr Pro Val Glu His Gly Leu Val Leu Pro
370                 375                 380

Ser Gly Pro Leu Ile His Gly Thr Gly Gly Tyr Gly Gly Met Asn
385                 390                 395                 400

Pro Pro Val Thr Asp Ala Pro Ala Pro Gln Val Pro Ala Arg Ala Gln
            405                 410                 415

Pro Met Thr Thr Ala Ala Glu His Thr Pro Ala Val Thr Gln Pro Gln
            420                 425                 430

His Thr Pro Val Glu Pro Pro Val His Asp Lys Pro Pro Ser His Ser
        435                 440                 445

Val Phe Asp Val Gly His Glu Pro Pro Val Thr His Thr Pro Pro Ala
    450                 455                 460

Pro Ile Glu Leu Pro Ser Tyr Gly Leu Phe Gly Leu Pro Gly Phe
465                 470                 475

<210> SEQ ID NO 37
<211> LENGTH: 388
<212> TYPE: PRT
<213> ORGANISM: Mycobacterium tuberculosis

<400> SEQUENCE: 37

Met Ala Phe Pro Arg Thr Leu Ala Ile Leu Ala Ala Ala Ala Leu
1               5                   10                  15

Val Val Ala Cys Ser His Gly Gly Thr Pro Thr Gly Ser Ser Thr Thr
            20                  25                  30

Ser Gly Ala Ser Pro Ala Thr Pro Val Ala Val Pro Val Pro Arg Ser
        35                  40                  45

```
Cys Ala Glu Pro Ala Gly Ile Pro Ala Leu Leu Ser Pro Arg Asp Lys
 50                  55                  60

Leu Ala Gln Leu Leu Val Val Gly Val Arg Asp Ala Asp Ala Gln
 65                  70                  75                  80

Ala Val Val Thr Asn Tyr His Val Gly Gly Ile Leu Ile Gly Ser Asp
                 85                  90                  95

Thr Asp Leu Thr Ile Phe Asp Gly Ala Leu Ala Glu Ile Val Ala Gly
                100                 105                 110

Gly Gly Pro Leu Pro Leu Ala Val Ser Val Asp Glu Gly Gly Arg
            115                 120                 125

Val Ser Arg Leu Arg Ser Leu Ile Gly Gly Thr Gly Pro Ser Ala Arg
130                 135                 140

Glu Leu Ala Gln Thr Arg Thr Val Gln Gln Val Arg Asp Leu Ala Arg
145                 150                 155                 160

Asp Arg Gly Arg Gln Met Arg Lys Leu Gly Ile Thr Ile Asp Phe Ala
                165                 170                 175

Pro Val Val Asp Val Thr Asp Ala Pro Asp Thr Val Ile Gly Asp
            180                 185                 190

Arg Ser Phe Gly Ser Asp Pro Ala Thr Val Thr Ala Tyr Ala Gly Ala
                195                 200                 205

Tyr Ala Gln Gly Leu Arg Asp Ala Gly Val Leu Pro Val Leu Lys His
210                 215                 220

Phe Pro Gly His Gly Arg Gly Ser Gly Asp Ser His Asn Gly Gly Val
225                 230                 235                 240

Thr Thr Pro Pro Leu Asp Asp Leu Val Gly Asp Asp Leu Val Pro Tyr
                245                 250                 255

Arg Thr Leu Val Thr Gln Ala Pro Val Gly Val Met Val Gly His Leu
                260                 265                 270

Gln Val Pro Gly Leu Thr Gly Ser Glu Pro Ala Ser Leu Ser Lys Ala
            275                 280                 285

Ala Val Asn Leu Leu Arg Thr Gly Thr Gly Tyr Gly Ala Pro Pro Phe
290                 295                 300

Asp Gly Pro Val Phe Ser Asp Asp Leu Ser Gly Met Ala Ala Ile Ser
305                 310                 315                 320

Asp Arg Phe Gly Val Ser Glu Ala Val Leu Arg Thr Leu Gln Ala Gly
                325                 330                 335

Ala Asp Ile Ala Leu Trp Val Thr Thr Lys Glu Val Pro Ala Val Leu
            340                 345                 350

Asp Arg Leu Glu Gln Ala Leu Arg Ala Gly Glu Leu Pro Met Ser Ala
            355                 360                 365

Val Asp Arg Ser Val Val Arg Val Ala Thr Met Lys Gly Pro Asn Pro
370                 375                 380

Gly Cys Gly Arg
385

<210> SEQ ID NO 38
<211> LENGTH: 615
<212> TYPE: PRT
<213> ORGANISM: Mycobacterium tuberculosis

<400> SEQUENCE: 38

Met Gly Lys Glu Arg Asn Met Gly Glu Ser Glu Arg Ser Glu Ala Phe
1               5                   10                  15

Gly Ile Pro Arg Asp Ser Pro Leu Ser Ser Gly Asp Ala Ala Glu Leu
            20                  25                  30
```

-continued

Glu Gln Leu Arg Arg Glu Ala Ala Val Leu Arg Gln Leu Glu Asn
            35                  40                  45

Ala Val Gly Ser His Ala Pro Thr Arg Ser Ala Arg Asp Ile His Gln
 50                  55                  60

Leu Glu Ala Arg Ile Asp Ser Leu Ala Ala Arg Asn Ser Lys Leu Met
 65                  70                  75                  80

Glu Thr Leu Lys Glu Ala Arg Gln Gln Leu Leu Ala Leu Arg Glu Glu
                85                  90                  95

Val Asp Arg Leu Gly Gln Pro Pro Ser Gly Tyr Gly Val Leu Leu Ala
                100                 105                 110

Thr His Asp Asp Asp Thr Val Asp Val Phe Thr Ser Gly Arg Lys Met
            115                 120                 125

Arg Leu Thr Cys Ser Pro Asn Ile Asp Ala Ala Ser Leu Lys Lys Gly
            130                 135                 140

Gln Thr Val Arg Leu Asn Glu Ala Leu Thr Val Val Glu Ala Gly Thr
145                 150                 155                 160

Phe Glu Ala Val Gly Glu Ile Ser Thr Leu Arg Glu Ile Leu Ala Asp
                165                 170                 175

Gly His Arg Ala Leu Val Val Gly His Ala Asp Glu Glu Arg Val Val
                180                 185                 190

Trp Leu Ala Asp Pro Leu Ile Ala Glu Asp Leu Pro Asp Gly Leu Pro
            195                 200                 205

Glu Ala Leu Asn Asp Asp Thr Arg Pro Arg Lys Leu Arg Pro Gly Asp
            210                 215                 220

Ser Leu Leu Val Asp Thr Lys Ala Gly Tyr Ala Phe Glu Arg Ile Pro
225                 230                 235                 240

Lys Ala Glu Val Glu Asp Leu Val Leu Glu Val Pro Asp Val Ser
                245                 250                 255

Tyr Ala Asp Ile Gly Gly Leu Ser Arg Gln Ile Glu Gln Ile Arg Asp
                260                 265                 270

Ala Val Glu Leu Pro Phe Leu His Lys Glu Leu Tyr Arg Glu Tyr Ser
            275                 280                 285

Leu Arg Pro Pro Lys Gly Val Leu Leu Tyr Gly Pro Pro Gly Cys Gly
            290                 295                 300

Lys Thr Leu Ile Ala Lys Ala Val Ala Asn Ser Leu Ala Lys Lys Met
305                 310                 315                 320

Ala Glu Val Arg Gly Asp Asp Ala His Glu Ala Lys Ser Tyr Phe Leu
                325                 330                 335

Asn Ile Lys Gly Pro Glu Leu Leu Asn Lys Phe Val Gly Glu Thr Glu
            340                 345                 350

Arg His Ile Arg Leu Ile Phe Gln Arg Ala Arg Glu Lys Ala Ser Glu
            355                 360                 365

Gly Thr Pro Val Ile Val Phe Phe Asp Glu Met Asp Ser Ile Phe Arg
            370                 375                 380

Thr Arg Gly Thr Gly Val Ser Ser Asp Val Glu Thr Thr Val Val Pro
385                 390                 395                 400

Gln Leu Leu Ser Glu Ile Asp Gly Val Glu Gly Leu Glu Asn Val Ile
                405                 410                 415

Val Ile Gly Ala Ser Asn Arg Glu Asp Met Ile Asp Pro Ala Ile Leu
            420                 425                 430

Arg Pro Gly Arg Leu Asp Val Lys Ile Lys Ile Glu Arg Pro Asp Ala
            435                 440                 445

```
Glu Ala Ala Gln Asp Ile Tyr Ser Lys Tyr Leu Thr Glu Phe Leu Pro
    450                 455                 460

Val His Ala Asp Asp Leu Ala Glu Phe Asp Gly Asp Arg Ser Ala Cys
465                 470                 475                 480

Ile Lys Ala Met Ile Glu Lys Val Val Asp Arg Met Tyr Ala Glu Ile
                485                 490                 495

Asp Asp Asn Arg Phe Leu Glu Val Thr Tyr Ala Asn Gly Asp Lys Glu
                500                 505                 510

Val Met Tyr Phe Lys Asp Phe Asn Ser Gly Ala Met Ile Gln Asn Val
            515                 520                 525

Val Asp Arg Ala Lys Lys Asn Ala Ile Lys Ser Val Leu Glu Thr Gly
530                 535                 540

Gln Pro Gly Leu Arg Ile Gln His Leu Leu Asp Ser Ile Val Asp Glu
545                 550                 555                 560

Phe Ala Glu Asn Glu Asp Leu Pro Asn Thr Thr Asn Pro Asp Asp Trp
                565                 570                 575

Ala Arg Ile Ser Gly Lys Lys Gly Glu Arg Ile Val Tyr Ile Arg Thr
                580                 585                 590

Leu Val Thr Gly Lys Ser Ser Ser Ala Ser Arg Ala Ile Asp Thr Glu
            595                 600                 605

Ser Asn Leu Gly Gln Tyr Leu
            610             615

<210> SEQ ID NO 39
<211> LENGTH: 102
<212> TYPE: PRT
<213> ORGANISM: Mycobacterium tuberculosis

<400> SEQUENCE: 39

Met Thr Leu Arg Val Val Pro Glu Gly Leu Ala Ala Ser Ala Ala
1               5                   10                  15

Val Glu Ala Leu Thr Ala Arg Leu Ala Ala Ala His Ala Ser Ala Ala
            20                  25                  30

Pro Val Ile Thr Ala Val Val Pro Ala Ala Asp Pro Val Ser Leu
            35                  40                  45

Gln Thr Ala Ala Gly Phe Ser Ala Gln Gly Val Glu His Ala Val Val
    50                  55                  60

Thr Ala Glu Gly Val Glu Glu Leu Gly Arg Ala Gly Val Gly Val Gly
65                  70                  75                  80

Glu Ser Gly Ala Ser Tyr Leu Ala Gly Ala Ala Ala Ala Thr
                85                  90                  95

Tyr Gly Val Val Gly Gly
            100

<210> SEQ ID NO 40
<211> LENGTH: 235
<212> TYPE: PRT
<213> ORGANISM: Mycobacterium tuberculosis

<400> SEQUENCE: 40

Met Ser Lys Thr Ser Lys Ala Tyr Arg Ala Ala Ala Lys Val Asp
1               5                   10                  15

Arg Thr Asn Leu Tyr Thr Pro Leu Gln Ala Lys Leu Ala Lys Glu
            20                  25                  30

Thr Ser Ser Thr Lys Gln Asp Ala Thr Val Glu Val Ala Ile Arg Leu
            35                  40                  45
```

```
Gly Val Asp Pro Arg Lys Ala Asp Gln Met Val Arg Gly Thr Val Asn
        50                  55                  60

Leu Pro His Gly Thr Gly Lys Thr Ala Arg Val Ala Val Phe Ala Val
 65                  70                  75                  80

Gly Glu Lys Ala Asp Ala Ala Val Ala Gly Ala Asp Val Val Gly
                 85                  90                  95

Ser Asp Asp Leu Ile Glu Arg Ile Gln Gly Gly Trp Leu Glu Phe Asp
                100                 105                 110

Ala Ala Ile Ala Thr Pro Asp Gln Met Ala Lys Val Gly Arg Ile Ala
                115                 120                 125

Arg Val Leu Gly Pro Arg Gly Leu Met Pro Asn Pro Lys Thr Gly Thr
130                 135                 140

Val Thr Ala Asp Val Ala Lys Ala Val Ala Asp Ile Lys Gly Gly Lys
145                 150                 155                 160

Ile Asn Phe Arg Val Asp Lys Gln Ala Asn Leu His Phe Val Ile Gly
                165                 170                 175

Lys Ala Ser Phe Asp Glu Lys Leu Leu Ala Glu Asn Tyr Gly Ala Ala
                180                 185                 190

Ile Asp Glu Val Leu Arg Leu Lys Pro Ser Ser Lys Gly Arg Tyr
                195                 200                 205

Leu Lys Lys Ile Thr Val Ser Thr Thr Thr Gly Pro Gly Ile Pro Val
210                 215                 220

Asp Pro Ser Ile Thr Arg Asn Phe Ala Gly Glu
225                 230                 235

<210> SEQ ID NO 41
<211> LENGTH: 728
<212> TYPE: PRT
<213> ORGANISM: Mycobacterium tuberculosis

<400> SEQUENCE: 41

Met Thr His Pro Asp Pro Ala Arg Gln Leu Thr Leu Thr Ala Arg Leu
 1               5                  10                  15

Asn Thr Ser Ala Val Asp Ser Arg Arg Gly Val Val Arg Leu His Pro
                 20                  25                  30

Asn Ala Ile Ala Ala Leu Gly Ile Arg Glu Trp Asp Ala Val Ser Leu
             35                  40                  45

Thr Gly Ser Arg Thr Thr Ala Val Ala Gly Leu Ala Ala Ala Asp
        50                  55                  60

Thr Ala Val Gly Thr Val Leu Leu Asp Asp Val Thr Leu Ser Asn Ala
 65                  70                  75                  80

Gly Leu Arg Glu Gly Thr Glu Val Ile Val Ser Pro Val Thr Val Tyr
                 85                  90                  95

Gly Ala Arg Ser Val Thr Leu Ser Gly Ser Thr Leu Ala Thr Gln Ser
                100                 105                 110

Val Pro Pro Val Thr Leu Arg Gln Ala Leu Leu Gly Lys Val Met Thr
                115                 120                 125

Val Gly Asp Ala Val Ser Leu Leu Pro Arg Asp Leu Gly Pro Gly Thr
130                 135                 140

Ser Thr Ser Ala Ala Ser Arg Ala Leu Ala Ala Val Gly Ile Ser
145                 150                 155                 160

Trp Thr Ser Glu Leu Leu Thr Val Thr Gly Val Asp Pro Asp Gly Pro
                165                 170                 175

Val Ser Val Gln Pro Asn Ser Leu Val Thr Trp Gly Ala Gly Val Pro
                180                 185                 190
```

```
Ala Ala Met Gly Thr Ser Thr Ala Gly Gln Val Ser Ile Ser Ser Pro
            195                 200                 205

Glu Ile Gln Ile Glu Glu Leu Lys Gly Ala Gln Pro Gln Ala Ala Lys
210                 215                 220

Leu Thr Glu Trp Leu Lys Leu Ala Leu Asp Glu Pro His Leu Leu Gln
225                 230                 235                 240

Thr Leu Gly Ala Gly Thr Asn Leu Gly Val Leu Val Ser Gly Pro Ala
            245                 250                 255

Gly Val Gly Lys Ala Thr Leu Val Arg Ala Val Cys Asp Gly Arg Arg
            260                 265                 270

Leu Val Thr Leu Asp Gly Pro Glu Ile Gly Ala Leu Ala Ala Gly Asp
            275                 280                 285

Arg Val Lys Ala Val Ala Ser Ala Val Gln Ala Val Arg His Glu Gly
            290                 295                 300

Gly Val Leu Leu Ile Thr Asp Ala Asp Ala Leu Leu Pro Ala Ala Ala
305                 310                 315                 320

Glu Pro Val Ala Ser Leu Ile Leu Ser Glu Leu Arg Thr Ala Val Ala
            325                 330                 335

Thr Ala Gly Val Val Leu Ile Ala Thr Ser Ala Arg Pro Asp Gln Leu
            340                 345                 350

Asp Ala Arg Leu Arg Ser Pro Glu Leu Cys Asp Arg Glu Leu Gly Leu
            355                 360                 365

Pro Leu Pro Asp Ala Ala Thr Arg Lys Ser Leu Leu Glu Ala Leu Leu
            370                 375                 380

Asn Pro Val Pro Thr Gly Asp Leu Asn Leu Asp Glu Ile Ala Ser Arg
385                 390                 395                 400

Thr Pro Gly Phe Val Val Ala Asp Leu Ala Ala Leu Val Arg Glu Ala
            405                 410                 415

Ala Leu Arg Ala Ala Ser Arg Ala Ser Ala Asp Gly Arg Pro Pro Met
            420                 425                 430

Leu His Gln Asp Asp Leu Leu Gly Ala Leu Thr Val Ile Arg Pro Leu
            435                 440                 445

Ser Arg Ser Ala Ser Asp Glu Val Thr Val Gly Asp Val Thr Leu Asp
            450                 455                 460

Asp Val Gly Asp Met Ala Ala Lys Gln Ala Leu Thr Glu Ala Val
465                 470                 475                 480

Leu Trp Pro Leu Gln His Pro Asp Thr Phe Ala Arg Leu Gly Val Glu
            485                 490                 495

Pro Pro Arg Gly Val Leu Leu Tyr Gly Pro Pro Gly Cys Gly Lys Thr
            500                 505                 510

Phe Val Val Arg Ala Leu Ala Ser Thr Gly Gln Leu Ser Val His Ala
            515                 520                 525

Val Lys Gly Ser Glu Leu Met Asp Lys Trp Val Gly Ser Ser Glu Lys
            530                 535                 540

Ala Val Arg Glu Leu Phe Arg Ala Arg Asp Ser Ala Pro Ser Leu
545                 550                 555                 560

Val Phe Leu Asp Glu Leu Asp Ala Leu Ala Pro Arg Arg Gly Gln Ser
            565                 570                 575

Phe Asp Ser Gly Val Ser Asp Arg Val Val Ala Ala Leu Leu Thr Glu
            580                 585                 590

Leu Asp Gly Ile Asp Pro Leu Arg Asp Val Val Met Leu Gly Ala Thr
            595                 600                 605
```

```
Asn Arg Pro Asp Leu Ile Asp Pro Ala Leu Leu Pro Gly Arg Leu
    610                 615                 620

Glu Arg Leu Val Phe Val Glu Pro Pro Asp Ala Ala Arg Arg Glu
625                 630                 635                 640

Ile Leu Arg Thr Ala Gly Lys Ser Ile Pro Leu Ser Ser Asp Val Asp
                645                 650                 655

Leu Asp Glu Val Ala Ala Gly Leu Asp Gly Tyr Ser Ala Ala Asp Cys
            660                 665                 670

Val Ala Leu Arg Glu Ala Ala Leu Thr Ala Met Arg Arg Ser Ile
                675                 680                 685

Asp Ala Ala Asn Val Thr Ala Ala Asp Leu Ala Thr Ala Arg Glu Thr
    690                 695                 700

Val Arg Ala Ser Leu Asp Pro Leu Gln Val Ala Ser Leu Arg Lys Phe
705                 710                 715                 720

Gly Thr Lys Gly Asp Leu Arg Ser
                725
```

```
<210> SEQ ID NO 42
<211> LENGTH: 83
<212> TYPE: PRT
<213> ORGANISM: Mycobacterium tuberculosis

<400> SEQUENCE: 42

Met Gly Ser Asp Cys Gly Cys Gly Gly Tyr Leu Trp Ser Met Leu Lys
1               5                   10                  15

Arg Val Glu Ile Glu Val Asp Asp Leu Ile Gln Lys Val Ile Arg
            20                  25                  30

Arg Tyr Arg Val Lys Gly Ala Arg Glu Ala Val Asn Leu Ala Leu Arg
        35                  40                  45

Thr Leu Leu Gly Glu Ala Asp Thr Ala Glu His Gly His Asp Asp Glu
    50                  55                  60

Tyr Asp Glu Phe Ser Asp Pro Asn Ala Trp Val Pro Arg Arg Ser Arg
65                  70                  75                  80

Asp Thr Gly
```

```
<210> SEQ ID NO 43
<211> LENGTH: 1021
<212> TYPE: PRT
<213> ORGANISM: Mycobacterium tuberculosis

<400> SEQUENCE: 43

Met Ala Gly Val Thr Arg Glu Ile Asn Leu Leu Ala Gln Ala Ser Gln
1               5                   10                  15

Trp Arg Arg Leu Gly Gly Thr Phe Pro Thr Asn Ser Gln Leu Thr Asn
            20                  25                  30

Glu Ser Ala Ala Ser Leu Arg Leu Tyr Ala Gln Leu Ile Asp Leu Leu
        35                  40                  45

Asp Met Val Val Asp Val Asp Ile Leu Ser Gly Thr Ser Ala Gly Gly
    50                  55                  60

Ile Asn Ala Ala Leu Leu Ala Ser Ser Arg Val Thr Gly Ser Asp Leu
65                  70                  75                  80

Gly Gly Ile Arg Asp Leu Trp Leu Asp Leu Gly Ala Leu Thr Glu Leu
                85                  90                  95

Leu Arg Asp Pro Arg Asp Lys Lys Thr Pro Ser Leu Leu Tyr Gly Asp
            100                 105                 110
```

```
Glu Arg Ile Phe Ala Ala Leu Ala Lys Arg Leu Pro Lys Leu Ala Thr
            115                 120                 125

Gly Pro Phe Pro Pro Thr Thr Phe Pro Glu Ala Arg Thr Pro Ser
130                 135                 140

Thr Thr Leu Tyr Ile Thr Thr Leu Leu Ala Gly Glu Thr Ser Arg
145                 150                 155                 160

Phe Thr Asp Ser Phe Gly Thr Leu Val Gln Asp Val Asp Leu Arg Gly
                165                 170                 175

Leu Phe Thr Phe Thr Glu Thr Asp Leu Ala Arg Pro Asp Thr Ala Pro
            180                 185                 190

Ala Leu Ala Leu Ala Ala Arg Ser Ser Ala Ser Phe Pro Leu Ala Phe
            195                 200                 205

Glu Pro Ser Phe Leu Pro Phe Thr Lys Gly Thr Ala Lys Lys Gly Glu
210                 215                 220

Val Pro Ala Arg Pro Ala Met Ala Pro Phe Thr Ser Leu Thr Arg Pro
225                 230                 235                 240

His Trp Val Ser Asp Gly Gly Leu Leu Asp Asn Arg Pro Ile Gly Val
                245                 250                 255

Leu Phe Lys Arg Ile Phe Asp Arg Pro Ala Arg Arg Pro Val Arg Arg
            260                 265                 270

Val Leu Leu Phe Val Val Pro Ser Ser Gly Pro Ala Pro Asp Pro Met
            275                 280                 285

His Glu Pro Pro Pro Asp Asn Val Asp Glu Pro Leu Gly Leu Ile Asp
            290                 295                 300

Gly Leu Leu Lys Gly Leu Ala Ala Val Thr Thr Gln Ser Ile Ala Ala
305                 310                 315                 320

Asp Leu Arg Ala Ile Arg Ala His Gln Asp Cys Met Glu Ala Arg Thr
                325                 330                 335

Asp Ala Lys Leu Arg Leu Ala Glu Leu Ala Ala Thr Leu Arg Asn Gly
            340                 345                 350

Thr Arg Leu Leu Thr Pro Ser Leu Leu Thr Asp Tyr Arg Thr Arg Glu
            355                 360                 365

Ala Thr Lys Gln Ala Gln Thr Leu Thr Ser Ala Leu Leu Arg Arg Leu
370                 375                 380

Ser Thr Cys Pro Pro Glu Ser Gly Pro Ala Thr Glu Ser Leu Pro Lys
385                 390                 395                 400

Ser Trp Ser Ala Glu Leu Thr Val Gly Gly Asp Ala Asp Lys Val Cys
                405                 410                 415

Arg Gln Gln Ile Thr Ala Thr Ile Leu Leu Ser Trp Ser Gln Pro Thr
            420                 425                 430

Ala Gln Pro Leu Pro Gln Ser Pro Ala Glu Leu Ala Arg Phe Gly Gln
            435                 440                 445

Pro Ala Tyr Asp Leu Ala Lys Gly Cys Ala Leu Thr Val Ile Arg Ala
450                 455                 460

Ala Phe Gln Leu Ala Arg Ser Asp Ala Asp Ile Ala Ala Leu Ala Glu
465                 470                 475                 480

Val Thr Glu Ala Ile His Arg Ala Trp Arg Pro Thr Ala Ser Ser Asp
                485                 490                 495

Leu Ser Val Leu Val Arg Thr Met Cys Ser Arg Pro Ala Ile Arg Gln
            500                 505                 510

Gly Ser Leu Glu Asn Ala Ala Asp Gln Leu Ala Ala Asp Tyr Leu Gln
            515                 520                 525
```

```
Gln Ser Thr Val Pro Gly Asp Ala Trp Glu Arg Leu Gly Ala Ala Leu
    530             535                 540
Val Asn Ala Tyr Pro Thr Leu Thr Gln Leu Ala Ala Ser Ala Ser Ala
545             550                 555                 560
Asp Ser Gly Ala Pro Thr Asp Ser Leu Leu Ala Arg Asp His Val Ala
                565                 570                 575
Ala Gly Gln Leu Glu Thr Tyr Leu Ser Tyr Leu Gly Thr Tyr Pro Gly
        580                 585                 590
Arg Ala Asp Asp Ser Arg Asp Ala Pro Thr Met Ala Trp Lys Leu Phe
    595                 600                 605
Asp Leu Ala Thr Thr Gln Arg Ala Met Leu Pro Ala Asp Ala Glu Ile
    610                 615                 620
Glu Gln Gly Leu Glu Leu Val Gln Val Ser Ala Asp Thr Arg Ser Leu
625             630                 635                 640
Leu Ala Pro Asp Trp Gln Thr Ala Gln Gln Lys Leu Thr Gly Met Arg
                645                 650                 655
Leu His His Phe Gly Ala Phe Tyr Lys Arg Ser Trp Arg Ala Asn Asp
        660                 665                 670
Trp Met Trp Gly Arg Leu Asp Gly Ala Gly Trp Leu Val His Val Leu
    675                 680                 685
Leu Asp Pro Arg Arg Val Arg Trp Ile Val Gly Glu Arg Ala Asp Thr
    690                 695                 700
Asn Gly Pro Gln Ser Gly Ala Gln Trp Phe Leu Gly Lys Leu Lys Glu
705             710                 715                 720
Leu Gly Ala Pro Asp Phe Pro Ser Pro Gly Tyr Pro Leu Pro Ala Val
                725                 730                 735
Gly Gly Gly Pro Ala Gln His Leu Thr Glu Asp Met Leu Leu Asp Glu
        740                 745                 750
Leu Gly Phe Leu Asp Asp Pro Ala Lys Pro Leu Pro Ala Ser Ile Pro
    755                 760                 765
Trp Thr Ala Leu Trp Leu Ser Gln Ala Trp Gln Gln Arg Val Leu Glu
    770                 775                 780
Glu Glu Leu Asp Gly Leu Ala Asn Thr Val Leu Asp Pro Gln Pro Gly
785             790                 795                 800
Lys Leu Pro Asp Trp Ser Pro Thr Ser Ser Arg Thr Trp Ala Thr Lys
                805                 810                 815
Val Leu Ala Ala His Pro Gly Asp Ala Lys Tyr Ala Leu Leu Asn Glu
        820                 825                 830
Asn Pro Ile Ala Gly Glu Thr Phe Ala Ser Asp Lys Gly Ser Pro Leu
    835                 840                 845
Met Ala His Thr Val Ala Lys Ala Ala Ala Thr Ala Gly Ala Ala
    850                 855                 860
Gly Ser Val Arg Gln Leu Pro Ser Val Leu Lys Pro Pro Leu Ile Thr
865             870                 875                 880
Leu Arg Thr Leu Thr Leu Ser Gly Tyr Arg Val Val Ser Leu Thr Lys
                885                 890                 895
Gly Ile Ala Arg Ser Thr Ile Ile Ala Gly Ala Leu Leu Leu Val Leu
        900                 905                 910
Gly Val Ala Ala Ala Ile Gln Ser Val Thr Val Phe Gly Val Thr Gly
    915                 920                 925
Leu Ile Ala Ala Gly Thr Gly Gly Leu Leu Val Val Leu Gly Thr Trp
    930                 935                 940
```

```
Gln Val Ser Gly Arg Leu Leu Phe Ala Leu Leu Ser Phe Ser Val Val
945                 950                 955                 960

Gly Ala Val Leu Ala Leu Ala Thr Pro Val Val Arg Glu Trp Leu Phe
                965                 970                 975

Gly Thr Gln Gln Gln Pro Gly Trp Val Gly Thr His Ala Tyr Trp Leu
            980                 985                 990

Gly Ala Gln Trp Trp His Pro Leu Val Val Val Gly Leu Ile Ala Leu
            995                 1000                1005

Val Ala Ile Met Ile Ala Ala Ala Thr Pro Gly Arg Arg
    1010                1015                1020

<210> SEQ ID NO 44
<211> LENGTH: 192
<212> TYPE: PRT
<213> ORGANISM: Mycobacterium tuberculosis

<400> SEQUENCE: 44

Met Asn Ile Arg Cys Gly Leu Ala Ala Gly Ala Val Ile Cys Ser Ala
1               5                   10                  15

Val Ala Leu Gly Ile Ala Leu His Ser Gly Asp Pro Ala Arg Ala Leu
                20                  25                  30

Gly Pro Pro Pro Asp Gly Ser Tyr Ser Phe Asn Gln Ala Gly Val Ser
            35                  40                  45

Gly Val Thr Trp Thr Ile Thr Ala Leu Cys Asp Gln Pro Ser Gly Thr
50                  55                  60

Arg Asn Met Asn Asp Tyr Ser Asp Pro Ile Val Trp Ala Phe Asn Cys
65                  70                  75                  80

Ala Leu Asn Val Val Ser Thr Thr Pro Gln Gln Ile Thr Arg Thr Asp
                85                  90                  95

Arg Leu Gln Asn Phe Ser Gly Arg Ala Arg Met Ser Ser Met Leu Trp
            100                 105                 110

Thr Phe Gln Val Asn Gln Ala Asp Gly Val Ala Cys Pro Asp Gly Ser
            115                 120                 125

Thr Ala Pro Ser Ser Glu Thr Tyr Ala Phe Ser Asp Glu Thr Leu Thr
130                 135                 140

Gly Thr His Thr Thr Val His Gly Ala Val Cys Gly Leu Gln Pro Lys
145                 150                 155                 160

Leu Ser Lys Gln Pro Phe Ser Leu Gln Leu Ile Gly Pro Pro Pro Ser
                165                 170                 175

Pro Val Gln Arg Tyr Pro Leu Tyr Cys Asn Asn Ile Ala Met Cys Tyr
            180                 185                 190
```

COMPOSITIONS COMPRISING SOLUBLE HLA/M. TUBERCULOSIS-SPECIFIC LIGAND COMPLEXES AND METHODS OF PRODUCTION AND USE THEREOF

CROSS REFERENCE TO RELATED APPLICATIONS/INCORPORATION BY REFERENCE STATEMENT

This application claims benefit under 35 USC 119(e) of U.S. Ser. No. 61/972,202, filed Mar. 28, 2014. The entire contents of the above-referenced patent application are hereby expressly incorporated herein by reference.

STATEMENT REGARDING FEDERALLY SPONSORED RESEARCH OR DEVELOPMENT

This invention was made with government support under Contract No. BAA-NIAID-DAIT-NIHAI2008032 awarded by the National Institutes of Health. The government has certain rights in this invention.

BACKGROUND

Class I major histocompatibility complex (MHC) molecules, designated class I HLA in humans, bind and display peptide antigen ligands upon the cell surface. The peptide antigen ligands presented by the class I MHC molecule are derived from either normal endogenous proteins ("self") or foreign proteins ("non-self") introduced into the cell. Non-self proteins may be products of malignant transformation or intracellular pathogens such as viruses. In this manner, class I MHC molecules convey information regarding the internal fitness of a cell to immune effector cells including but not limited to, $CD8^+$ cytotoxic T lymphocytes (CTLs), which are activated upon interaction with "non-self" peptides, thereby lysing or killing the cell presenting such "non-self" peptides.

Class I HLA molecules exhibit extensive polymorphism generated by systematic recombinatorial and point mutation events; as such, hundreds of different HLA types exist throughout the world's population, resulting in a large immunological diversity. Such extensive HLA diversity throughout the population results in tissue or organ transplant rejection between individuals as well as differing susceptibilities and/or resistances to infectious diseases. HLA molecules also contribute significantly to autoimmunity and cancer. Because HLA molecules mediate most, if not all, adaptive immune responses, large quantities of pure isolated HLA proteins are required in order to effectively study transplantation, autoimmunity disorders, and for vaccine development.

Class I MHC molecules alert the immune response to disorders within host cells. Peptides, which are derived from viral- and tumor-specific proteins within the cell, are loaded into the class I MHC molecule's antigen binding groove in the endoplasmic reticulum of the cell and subsequently carried to the cell surface. Once the class I MHC molecule and its loaded peptide ligand are on the cell surface, the class I MHC molecule and its peptide ligand are accessible to cytotoxic T lymphocytes (CTL). CTL survey the peptides presented by the class I MHC molecule and destroy those cells harboring ligands derived from infectious or neoplastic agents within that cell.

Discerning disease-specific class I MHC ligands for CTL recognition is an important component of immunotherapy design. Ligands unique to infected cells can be tested and incorporated into vaccines designed to evoke a protective CTL response. Several methodologies are currently employed to identify potentially protective peptide ligands. One approach uses T cell lines or clones to screen for biologically active ligands among chromatographic fractions of eluted peptides (Cox et al. (1994) Science, 264:716-719, which is expressly incorporated herein by reference in its entirety). This approach has been employed to identify peptide ligands specific to cancerous or infected cells. A second technique utilizes predictive algorithms to identify peptides capable of binding to a particular class I MHC molecule based upon previously determined motif and/or individual ligand sequences (DeGroot et al. (2001) Emerging Infectious Diseases, 7:4, which is expressly incorporated herein by reference in its entirety). Peptides having high predicted probability of binding from a pathogen of interest can then be synthesized and tested for T cell reactivity in various assays, such as but not limited to, precursor, tetramer, and ELISpot assays.

*Mycobacterium tuberculosis* (Mtb) is a pathogenic bacterial species and the cause of most cases of tuberculosis (TB). There are close to two-million estimated deaths annually resulting from TB infection. Current TB vaccines are effective at protecting against the disease during childhood, but there is no consistent protection against the contraction of pulmonary TB in adult. Thus, there exists a need to create a more effective vaccine against TB.

The non-classical HLA-E complex is distinct from classical HLA (such as HLA-A, HLA-B, and HLA-C) in that it is monomorphic in the human population, as compared with the classical HLA that are polymorphic. As such, all people in the population tend to have the same HLA-E on the surface of all their cells. Additionally, HLA-E provides a very specialized immune function that involves presentation of classical HLA leader sequences to inhibit NK cell function. Apart from this specialized function, HLA-E is thought to act like a classical class I HLA by presenting *M. tuberculosis*-derived peptide ligands to T-cells. However, this is unclear, and it is primarily known that HLA-E presents leader peptides from other proteins. Thus, identifying Mtb-derived peptide ligands that are made available by the HLA-E of Mtb-infected cells would be novel and of great value.

A number of potential strategies exist to identify Mtb peptide sequences that are presented by the HLA of Mtb-infected cells. In addition to those methods described herein above, HLA molecules isolated from cell lysates of pathogen-infected cells are also currently used to identify class I HLA-presented peptides; these methods, however, result in low peptide yields and/or relatively impure samples, and impurity and low concentrations lead to poor data. In addition, these current methods provide ambiguity as to which HLA allele is presenting said peptides; therefore, which HLA/peptide complex actually marks the surface of infected cells for targeting or diagnostics remains difficult to ascertain.

Many peptide ligands derived from Mtb have been reported in the context of classical HLA (i.e., HLA-A, HLA-B, and HLA-C). However, all Mtb-derived peptide ligands have been reported in the context of a non-classical HLA such as HLA-E. In addition, no previous reports of HLA-presented Mtb ligands have been reported in polymorphic HLA that differ from person to person, and thus the downstream diagnostics and therapies will only work on a subset of the population.

Therefore, there exists a need in the art for new and improved diagnostic and treatment methods for Mtb and identification of Mtb peptide ligands that are presented by the HLA of Mtb-infected cells, and particularly (but not limited to) the HLA-E of Mtb-infected cells. It is to such methods, peptide sequences, and compositions containing such peptide sequences, that the presently disclosed and/or claimed inventive concept(s) is directed.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1 graphically illustrates the deep ligand sequencing workflow utilized in accordance with the presently disclosed and/or claimed inventive concept(s), whereby sHLA (such as but not limited to, sHLA-E) was gathered from uninfected cells and cells infected with *M. tuberculosis*. The sHLA was purified, and the peptide pool was collected from the sHLA after acid elution. The directly eluted peptides were fractionated at high pH. The peptide rich fractions were then separated at low pH and directly injected into a mass spectrometer (such as, but not limited to, the TRIPLETOF® 5600+ mass spectrometer (AB Sciex Pte. Ltd., Framingham, Mass.)). MSI ion maps from Mtb-infected cells were compared to maps from the uninfected cells, and high throughput ion specific MS2 fragmentation was completed. A suite of software packages assigned sequences from the MS2 fragment spectra that were both unique to the infected cell and derived from Mtb. These Mtb sequences were validated with MS2 fragmentation of a corresponding synthetic peptide.

DETAILED DESCRIPTION

Before explaining at least one embodiment of the presently disclosed and/or claimed inventive concept(s) in detail by way of exemplary drawings, experimentation, results, and laboratory procedures, it is to be understood that the presently disclosed and/or claimed inventive concept(s) is not limited in its application to the details of construction and the arrangement of the components set forth in the following description or illustrated in the drawings, experimentation and/or results. The presently disclosed and/or claimed inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2nd ed., Cold Spring Harbor Laboratory Press, Cold Spring Harbor, N.Y. (1989) and Coligan et al. Current Protocols in Immunology (Current Protocols, Wiley Interscience (1994)), which are incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

All patents, published patent applications, and non-patent publications mentioned in the specification are indicative of the level of skill of those of ordinary skill in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed and/or claimed herein can be made and executed without undue experimentation in light of the present disclosure. While the compositions and methods of the inventive concept(s) have been described in terms of particular embodiments, it will be apparent to those of ordinary skill in the art that variations may be applied to the compositions and/or methods and in the steps or in the sequence of steps of the method described herein without departing from the concept, spirit and scope of the presently disclosed and/or claimed inventive concept(s). All such similar substitutes and modifications apparent to those of ordinary skill in the art are deemed to be within the spirit, scope and concept of the inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The singular forms "a," "an," and "the" include plural referents unless the context clearly indicates otherwise. Thus, for example, reference to "a compound" may refer to 1 or more, 2 or more, 3 or more, 4 or more or greater numbers of compounds. The term "plurality" refers to "two or more." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by ±20% or ±10%, or ±5%, or ±1%, or ±0.1% from the specified value, as such variations are appropriate to perform the disclosed methods and as understood by persons having ordinary skill in the art. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the terms "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The ordinary skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The terms "*M. tuberculosis*-specific" and "Mtb-specific" are used interchangeably herein and refer to HLA peptide epitopes that have been identified as being displayed in the context of HLA molecules on *Mycobacterium tuberculosis* (Mtb)-infected cells but not on cells which were not infected with Mtb. However, the terms "*M. tuberculosis*-specific" and "Mtb-specific" are not to be construed to mean that an HLA peptide epitope is limited to Mtb; indeed, multiple HLA peptide epitopes have been identified as being associated with other disease/infection states.

The presently disclosed and/or claimed inventive concept(s) relates generally to the identification of Mtb-derived peptide sequences that are presented by the HLA (such as, but not limited to, the HLA-E) of Mtb-infected cells. In the presently disclosed and/or claimed methods, milligram quantities of soluble HLA from cells that were infected with Mtb were harvested, and all the peptides ligands bound by the HLA of Mtb-infected cells were purified. Two-dimensional LCMS was then used to identify and sequence many of the peptide ligands presented by HLA. The use of soluble HLA in accordance with the presently disclosed and/or claimed inventive concept(s) provides a very pure preparation of peptides for HLA at a high concentration. This HLA ligand purity and concentration, in turn, allows the presently disclosed and/or claimed inventive concept(s) to supercede the sensitivity of other methods (biologic examples using a T-cell for example), and provides high-confidence HLA ligand sequences, thereby overcoming the defects and disadvantages of the prior art.

In particular (but not by way of limitation), Mtb peptide biomarkers presented by the HLA-E of Mtb-infected cells have been identified in accordance with the presently disclosed and/or claimed inventive concept(s). The HLA-E/Mtb ligands described and/or claimed herein were not previously known to be presented by the HLA-E of any infected cell. Because these HLA-E-presented Mtb peptides were purified and identified directly from infected cells, the presently disclosed and/or claimed inventive concept(s) has directly established that these HLA-E/Mtb complexes can be used as biomarkers of an infected cell, and targeted therapies can be developed based thereon. Additionally, since HLA-E is monomorphic, these targets can be applied to the entire human population. The HLA/ligand complexes discovered by direct comparison utilize soluble HLA molecules created in vitro. The soluble HLA molecules that enable direct comparative discovery of infected ligands do not exist in nature—these soluble HLA have been created in the laboratory. Therefore, the soluble HLA/ligand complexes distinct to Mtb-infected cells disclosed and/or claimed herein do not exist in nature.

The presently disclosed and/or claimed inventive concept(s) are based on a combination of methodologies for (1) the production of individual, soluble MHC molecules, and (2) epitope discovery and comparative ligand mapping methods (including methods of distinguishing infected cells from uninfected cells). The methods of production of individual, soluble MHC molecules have previously been described in detail in U.S. Pat. No. 7,521,202, issued Apr. 21, 2009, to Hildebrand et al., while the methods of epitope discovery and comparative ligand mapping have previously been described in detail in U.S. Pat. No. 7,541,429, issued Jun. 2, 2009, to Hildebrand et al. The entire contents of the above-referenced patents are expressly incorporated herein by reference. A brief description of each of these methodologies is included herein below for the purposes of exemplification and should not be considered as limiting.

In the methods of production of individual, soluble class I MHC molecule-endogenous peptide complexes (sMHC), a construct encoding a truncated, soluble form of an individual class I MHC molecule is transfected into a cell line that is able to naturally process proteins into peptide ligands capable of being loaded into antigen binding grooves of class I MHC molecules. The cell line is then cultured under conditions which allow for expression of the individual soluble class I MHC molecules from the construct, and these conditions also allow for endogenous loading of a peptide ligand into the antigen binding groove of each individual soluble class I MHC molecule prior to secretion of the individual soluble class I MHC molecules from the cell. The secreted individual soluble class I MHC molecules having the endogenously loaded peptide ligands bound thereto are then isolated. The construct that encodes the individual soluble class I MHC molecule may further encode a tag, such as (but not limited to) a HIS tail, a FLAG tail, or a VLDL tail, which is attached to the individual soluble class I MHC molecule and aids in isolating the individual soluble class I MHC molecule.

The methods of epitope discovery and comparative ligand mapping may be utilized to identify a peptide of interest that is associated with an infected state; in the method, at least one endogenously loaded peptide ligand is identified that distinguishes an infected cell from an uninfected cell, and said method utilizes the sMHC production technology described herein above. Any commercially available cell line (infected or uninfected) and/or lab created cell line (infected or uninfected) may be utilized, so long as the cell line is able to naturally process proteins into peptide ligands and is capable of loading these peptide ligands into antigen binding grooves of the soluble class I MHC molecules. For example (but not by way of limitation), (i) readily available, immortalized, uninfected cells line(s) and (ii) readily available infected cell line(s) from the same tissue/organ as the uninfected cell lines may be utilized; when commercially available cell lines are used, the two cell lines are infected with the construct encoding an individual soluble class I MHC molecule as described herein above with respect to the method of production of sMHC. Alternatively, the infected cell line may be produced from an uninfected cell line that already contains a construct that encodes an individual soluble class I MHC molecule. A portion of the uninfected cell line may become infected by any method known in the art or otherwise contemplated herein (such as, but not limited to, transfection with a construct encoding a gene).

The uninfected cell line and the infected cell line are each cultured under conditions which allow for expression of individual soluble class I MHC molecules from the construct. The culture conditions also allow for endogenous loading of a peptide ligand in the antigen binding groove of each individual soluble class I MHC molecule prior to secretion of the individual soluble class I MHC molecules from the cell. The secreted individual soluble class I MHC molecules having the endogenously loaded peptide ligands bound thereto are isolated from the uninfected cell line and the infected cell line, and the endogenously loaded peptide ligands are separated from the individual soluble class I MHC molecules from both the uninfected cell line and the infected cell line. The endogenously loaded peptide ligands are then isolated from both the uninfected cell line and the infected cell line, and the two sets of endogenously loaded peptide ligands are compared to identify at least one endogenously loaded peptide ligand presented by the individual soluble class I MHC molecule that distinguishes the infected cell line from the uninfected cell line.

The comparison of the two sets of peptide ligands may identify: (1) at least one peptide ligand presented on the infected cell line that is not presented on the uninfected cell line; (2) at least one peptide ligand presented in a substantially greater amount on the infected cell line when compared to the uninfected cell line; (3) at least one peptide ligand presented on the uninfected cell line that is not presented on the infected cell line; and/or (4) at least one peptide ligand that is presented in a substantially greater amount on the uninfected cell line when compared to the infected cell line. The term "substantially greater amount" as used herein refers to an amount that is detectably greater than another amount; for example, the term "presented in a substantially greater amount" as used herein refers to an at least one-fold increase in a first amount of presentation when compared to a second amount of presentation, such as but not limited to, an at least two-fold increase, an at least three-fold increase, an at least four-fold increase, an at least five-fold increase, an at least six-fold increase, an at least seven-fold increase, an at least eight-fold increase, an at least nine-fold increase, an at least ten-fold increase, an at least 20-fold increase, an at least 30-fold increase, an at least 40-fold increase, an at least 50-fold increase, an at least 100-fold increase, and the like.

Following identification of the peptide ligand that distinguishes an infected cell from an uninfected cell, a source protein from which the endogenously loaded peptide ligand is obtained can be identified. Such source protein may be encoded by the microorganism and/or the gene from the microorganism with which the cell line was infected to form the infected cell line, or the source protein may be encoded by the uninfected cell line. When the source protein is encoded by the uninfected cell line, such protein may also demonstrate increased expression in an Mtb-infected cell line.

The presently disclosed and/or claimed inventive concept(s) includes at least one isolated peptide ligand for an individual class I MHC molecule that has been isolated by the methods described herein. In one embodiment, the isolated peptide ligand(s) distinguishes an Mtb-infected cell from an uninfected cell, and thus is designated as an Mtb-specific peptide ligand herein. The isolated peptide ligand(s) may be an endogenously loaded peptide ligand presented by an individual class I MHC molecule that is unique to Mtb-infected cells when compared to cells not infected with Mtb.

Certain particular, non-limiting embodiments of the presently disclosed and/or claimed inventive concept(s) are directed to an isolated Mtb-specific peptide ligand comprising at least one sequence selected from the group consisting of SEQ ID NOS:1-29. In another embodiment, the isolated peptide ligand consists essentially of at least one sequence selected from the group consisting of SEQ ID NOS:1-29. The isolated Mtb-specific peptide ligand may consist essentially of a fragment of a source protein of one of SEQ ID NOS:30-44 (as outlined in Table 1) and comprise at least one sequence selected from the group consisting of SEQ ID NOS:1-29 (based on the relationship between peptide ligands and source proteins indicated in Table 1).

The length of the isolated Mtb-specific peptide ligand may be (for example, but not by way of limitation) from about 8 to about 20 amino acids. In addition, the isolated Mtb-specific peptide ligand may be for an HLA-E allele, such as but not limited to, HLA-E*01:01, HLA-E*01:03, HLA-E*01:04, HLA-E*01:05, HLA-E*01:06, and HLA-E*01:07. In particular, non-limiting embodiments, the isolated Mtb-specific peptide ligand is for HLA-E*01:01 or HLA-E*01:03.

In certain, non-limiting embodiments, the peptide ligands of the presently disclosed and/or claimed inventive concept(s) may be isolated by a method that includes providing a cell line containing a construct that encodes an individual soluble class I MHC molecule, wherein the cell line is able to naturally process proteins into peptide ligands capable of being loaded into antigen binding grooves of class I MHC molecules. The cell line is cultured under conditions which allow for expression of the individual soluble class I MHC molecules from the construct, and also allow for endogenous loading of a peptide ligand into the antigen binding groove of each individual soluble class I MHC molecule prior to secretion of the individual soluble class I MHC molecules from the cell. Secreted individual soluble class I MHC molecules having the endogenously loaded peptide ligands bound thereto are then isolated, and the peptide ligands are then separated from the individual soluble class I MHC molecules.

In another non-limiting embodiment, the isolated Mtb-specific peptide ligands of the presently disclosed and/or claimed inventive concept(s) may be identified by a method that includes providing uninfected and Mtb-infected cell lines, each containing the same construct that encodes an individual soluble class I MHC molecule, wherein the two cell lines are able to naturally process proteins into peptide ligands capable of being loaded into antigen binding grooves of class I MHC molecules. The two cell lines are each cultured under conditions which allow for expression of the individual soluble class I MHC molecules from the construct and also allow for endogenous loading of a peptide ligand in the antigen binding groove of each individual soluble class I MHC molecule prior to secretion of the individual soluble class I MHC molecules from the cell. The secreted individual soluble class I MHC molecules having the endogenously loaded peptide ligands bound thereto are isolated separately from the two cell lines, and endogenously loaded peptide ligands are separated from the individual soluble class I MHC molecules for each of the two separate pools. The endogenously loaded peptide ligands obtained from the two cell lines are then isolated and compared to one another. Finally, at least one endogenously loaded peptide ligand presented by the individual soluble class I MHC molecule is identified that distinguishes between the two cell lines; the peptide ligand may be unique to one of the two cell lines, or the peptide ligand may be presented in a substantially greater amount on one cell line when compared to the other cell line.

The utility of the identified MHC/HLA-presented peptide epitopes which mark the Mtb-infected cell is three-fold. First, diagnostics designed to detect Mtb can use epitopes unique to Mtb-infected cells to ascertain the presence/absence of an infection. Second, peptides unique to Mtb-infected cells represent vaccine candidates. Third, the entire HLA trimolecular complex containing the Mtb-specific peptide epitope represents a possible therapeutic target. For example, but not by way of limitation, the presently disclosed and/or claimed inventive concept(s) describes and claims multiple peptide epitopes that are either unique to or presented in substantially greater amounts on Mtb-infected cells. Also, as demonstrated herein below, such epitopes are unlikely to be predicted without direct epitope discovery. These Mtb-specific peptides can be used for vaccine development, and the unique Mtb-specific peptide/HLA complex can be utilized for diagnostics and/or specific targeting.

Other particular, non-limiting embodiments of the presently disclosed and/or claimed inventive concept(s) are directed to compositions that comprise at least one isolated class I MHC/HLA trimolecular complex formed in vitro. The trimolecular complex includes a soluble, truncated HLA-E heavy chain that does not contain the transmembrane and cytoplasmic domains of the native, full length HLA-E heavy chain. The trimolecular complex also includes beta-2-microglobulin and an Mtb-specific peptide ligand as described in detail herein above.

The soluble, truncated HLA-E heavy chain of the trimolecular complex may be a soluble, recombinantly produced HLA-E heavy chain. For example, the at least one isolated class I MHC/HLA trimolecular complex may be produced in a host cell made recombinant by a construct encoding the soluble, truncated HLA-E heavy chain, wherein the construct does not encode the transmembrane and cytoplasmic domains of the native, full length HLA-E heavy chain. In certain embodiments, the peptide is an endogenous peptide that is produced by the host cell and loaded in the trimolecular complex by the host cell. Alternatively, the peptide may be a synthetic peptide; the synthetic peptide (or a gene encoding same) may be introduced into the host cell for in vivo loading into the trimolecular complex, or the synthetic peptide may be mixed in vitro with the soluble, truncated HLA-E heavy chain and beta-2-microglobulin to form the trimolecular complex. Such methods of producing trimolecular complexes are well known in the art, and thus no further description thereof is deemed necessary.

In certain non-limiting embodiments, the composition may include at least two, at least three, at least four, at least five, at least six, at least seven, at least eight, at least nine, at least ten, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, or more isolated class I MHC/HLA trimolecular complexes as defined herein above. When multiple complexes are present, they may be unattached to one another, or they may be multimerized.

Thus, the compositions of the presently disclosed and/or claimed inventive concept(s) may include a multimer of isolated class I MHC/HLA trimolecular complexes. The term "multimer" as used herein will be understood to include two or more class I MHC/HLA-Mtb-specific epitope trimolecular complexes which are covalently or non-covalently attached together, either directly or indirectly. Each of the plurality of complexes present in the multimer may be multimerized by attachment to at least one other complex by any covalent or non-covalent method known in the art or otherwise contemplated herein.

If necessary, one or more of the class I MHC/HLA-Mtb-specific epitope trimolecular complexes present in a multimer may be modified in some manner known in the art to enable attachment of the complexes to each other; alternatively, the multimer may be formed around a substrate to which each trimolecular complex is attached. A tail may be attached to a portion of one or more of the trimolecular complexes to aid in multimerization; examples of tails that may be utilized include, but are not limited to, a biotinylation signal peptide tail, an immunoglobulin heavy chain tail, a TNF tail, an IgM tail, a leucine zipper, a Fos/Jun tail, combinations thereof, and the like. The multimer can contain any desired number of trimolecular complexes and thus form any multimer desired, such as but not limited to, a dimer, a trimer, a tetramer, a pentamer, a hexamer, and the like. Streptavidin has four binding sites for biotin, so a BSP (biotinylation signal peptide) tail may be attached to a portion of the HLA molecule during production thereof, and a tetramer of the desired trimolecular complex(es) could be formed by combining the trimolecular complexes having the BSP tails with biotin added enzymatically in vitro. An immunoglobulin heavy chain tail may be utilized as a substrate for forming a dimer, while a TNF tail may be utilized as a substrate for forming a trimer. An IgM tail could be utilized as a substrate for forming various combinations, such as tetramers, hexamers, and pentamers. In addition, the trimolecular complexes may be multimerized through liposomal encapsulation or artificial antigen presenting cell technology (see US Patent Application Publication No. 2002/0122820, published to Hildebrand et al. on Sep. 5, 2002, the contents of which are hereby expressly incorporated herein by reference). Further, the soluble HLA class II trimolecular complexes may be multimerized through the use of polymerized streptavidin and would produce what is termed a "STREPTAMER™" (IBA GmbH, Gottingen, Germany).

When the composition comprises a dimer of class I HLA trimolecular complexes, the peptides of the two trimolecular complexes may be the same or different. When the composition comprises a multimer of three or more class I HLA trimolecular complexes (such as but not limited to, a trimer, a tetramer, a pentamer, a hexamer, a heptamer, an octamer, and the like), all of the peptides of the trimolecular complexes present in the multimer may be the same, at least one of the peptides of the trimolecular complexes present in the multimer may be different, or all of the peptides of the trimolecular complexes present in the multimer may be different.

The trimolecular complexes of the presently disclosed and/or claimed inventive concept(s) may further be modified for providing better performance and/or for aiding in stabilization of the monomer or multimer. Examples of modifications that may be utilized in accordance with the presently disclosed and/or claimed inventive concept(s) include, but are not limited to, modifying an anchor and/or tail attached to the trimolecular complex as described herein above, modifying one or more amino acids in the Mtb-specific peptide/HLA trimolecular complex, PEGylation, chemical cross-linking, changes in pH or salt (depending on the specific peptide of the trimolecular complex), addition of one or more chaperone proteins that stabilize certain trimolecular complexes, combinations thereof, and the like.

Particular, non-limiting embodiments of the compositions of the presently disclosed and/or claimed inventive concept(s) include at least one isolated class I HLA trimolecular complex formed in vitro, wherein the trimolecular complex comprises the soluble, truncated HLA-E heavy chain as described herein above, beta-2-microglobulin, and a peptide selected from the following: (a) a peptide comprising SEQ ID NO:1; (b) a peptide comprising SEQ ID NO:2 and/or 3; (c) a peptide comprising SEQ ID NO:4; (d) a peptide comprising SEQ ID NO:5; (e) a peptide comprising at least one of SEQ ID NOS:6-9; (f) a peptide comprising SEQ ID NO:10 and/or 11; (g) a peptide comprising SEQ ID NO:12 and/or 13; (h) a peptide comprising SEQ ID NO:14; (i) a peptide comprising SEQ ID NO:15; (j) a peptide comprising SEQ ID NO:16; (k) a peptide comprising at least one of SEQ ID NOS:17-20; (l) a peptide comprising SEQ ID NO:21; (m) a peptide comprising SEQ ID NO:22; (n) a peptide comprising SEQ ID NO:23 and/or 24; (o) a peptide comprising SEQ ID NO:25 and/or 26; (p) a peptide comprising SEQ ID NO:27; (q) a peptide comprising SEQ ID NO:28; and (r) a peptide comprising SEQ ID NO:29.

Other particular, non-limiting embodiments of the compositions of the presently disclosed and/or claimed inventive concept(s) include at least one isolated class I HLA trimolecular complex formed in vitro, wherein the trimolecular complex comprises the soluble, truncated HLA-E heavy chain as described herein above, beta-2-microglobulin, and a peptide selected from the following: (a) a peptide consisting essentially of a fragment of SEQ ID NO:30 and comprising SEQ ID NO:1; (b) a peptide consisting essentially of a fragment of SEQ ID NO:31 and comprising SEQ ID NO:2 and/or 3; (c) a peptide consisting essentially of a fragment of SEQ ID NO:31 and comprising SEQ ID NO:4; (d) a peptide consisting essentially of a fragment of SEQ ID NO:31 and comprising SEQ ID NO:5; (e) a peptide consisting essentially of a fragment of SEQ ID NO:32 and comprising at least one of SEQ ID NOS:6-9; (f) a peptide consisting essentially of a fragment of SEQ ID NO:32 and comprising SEQ ID NO:10 and/or 11; (g) a peptide consisting essentially of a fragment of SEQ ID NO:33 and comprising SEQ ID NO:12 and/or 13; (h) a peptide consisting essentially of a fragment of SEQ ID NO:34 and comprising SEQ ID NO:14; (i) a peptide consisting essentially of a fragment of SEQ ID NO:35 and comprising SEQ ID NO:15; (j) a peptide consisting essentially of a fragment of SEQ ID NO:36 and comprising SEQ ID NO:16; (k) a peptide consisting essentially of a fragment of SEQ ID NO:37 and comprising at least one of SEQ ID NOS:17-20; (l) a peptide consisting essentially of a fragment of SEQ ID NO:38 and comprising SEQ ID NO:21; (m) a peptide consisting essentially of a fragment of SEQ ID NO:39 and comprising SEQ ID NO:22; (n) a peptide consisting essentially of a fragment of SEQ ID NO:40 and comprising SEQ ID NO:23 and/or 24; (o) a peptide consisting essentially of a fragment of SEQ ID NO:41 and comprising SEQ ID NO:25 and/or 26; (p) a peptide consisting essentially of a fragment of SEQ ID NO:42 and comprising SEQ ID NO:27; (q) a peptide consisting essentially of a fragment of SEQ ID NO:43 and comprising SEQ ID NO:28; and (r) a peptide consisting essentially of a fragment of SEQ ID NO:44 and comprising SEQ ID NO:29.

In addition, any of the components of the trimolecular complex may be provided in their peptide/polypeptide form or as a polynucleotide encoding the peptide/polypeptide form. Thus, another particular, non-limiting embodiment of the presently disclosed and/or claimed inventive concept(s) is directed to an isolated composition that includes (i) a soluble, truncated class I HLA-E heavy chain as described herein above or DNA encoding the soluble, truncated HLA-E heavy chain; (b) beta-2-microglobulin or DNA encoding beta-2-microglobulin; and (c) at least one Mtb-specific peptide ligand as described herein above, or DNA encoding the at least one peptide.

EXAMPLES

Examples are provided hereinbelow. However, the presently disclosed and/or claimed inventive concept(s) is to be understood to not be limited in its application to the specific experimentation, results and laboratory procedures. Rather, the Examples are simply provided as one of various embodiments and are meant to be exemplary, not exhaustive.

Example 1: Identification of Mtb-Specific HLA-E Peptide Epitopes

The identification of novel, Mtb-specific epitopes is a critical step in the development of T cell receptor-mediated immunotherapeutics against TB. To convey intracellular health to the immune system, mammals utilize the major histocompatibility complex (MHC) class I molecule. Class I MHC molecules are nature's proteome scanning chip. The class I MHC molecules gather many small peptides of intracellular origin, including the products of proteasomal processing and of defective translation, and carry these intracellular peptides to the cell surface. Intracellular peptides derived from proteins found in multiple compartments within the cell, and derived from proteins of many cellular functions, are sampled and presented at the cell surface by class I MHC. Immune cells, including but not limited to $CD8^+$ cytotoxic T-lymphocytes (CTL), survey the peptides presented by class I MHC and target cells displaying Mtb-specific peptides. Therefore, class I MHC-presented peptides distinguish and promote the recognition of infected cells by the adaptive immune system.

Given that class I MHC molecules distinguish infected cells from healthy cells, a number of studies have aimed to identify class I MHC-presented Mtb antigens. Because class I MHC molecules can be difficult to produce and purify, immune-based studies using CTL raised to autologous tumors have been utilized to identify Mtb immune targets. Other immune-based methods have relied upon predictive algorithms and in vitro class I MHC peptide binding assays. Although these indirect approaches have identified putative tumor antigens, a direct proteomics-based approach for identifying class I MHC Mtb-specific antigens is needed.

In addition, classic HLA (-A, -B, -C, and -G) are polymorphic; thus, in a diagnostic assay testing for the presence of Mtb, results based on peptides from classical HLA can lead to a large amount of variation in test results. Accordingly, a set of HLA-E binding peptides have been discovered by the methods described herein which are monomorphic in nature and would result in a superior assay or potential therapeutic.

Recognizing the protein production, isolation, and characterization challenges associated with the direct analysis of class I MHC proteome scanning chips, the presently disclosed and/or claimed inventive concept(s) utilized a method to obtain plentiful quantities of individual human class I MHC (HLA) from well-characterized Mtb-infected cell lines. Through expression of a secreted human class I MHC (sHLA) as described in U.S. Pat. No. 7,521,202 (incorporated supra and discussed in detail herein above), the cell's own class I HLA complexes remain on the cell surface, and only the transfected sHLA is harvested. Moreover, secretion of the human class I MHC molecule allows purification of the desired protein from tissue culture supernatants rather than requiring isolation of class I MHC from more complex detergent lysates.

The methodology of comparative ligand mapping as described in U.S. Pat. No. 7,541,429 (incorporated supra and discussed in detail herein above) and as illustrated in FIG. 1 was utilized herein to identify HLA-E*01:03 epitopes that were unique to Mtb-infected cells. The uninfected cell line and the Mtb-infected cell line were each transfected with a construct encoding HLA-E*01:03, as described herein above and in U.S. Pat. No. 7,521,202 (incorporated supra). The class I HLA-E*01:03 allele was selected for its high frequency in the population.

The uninfected cell line and the Mtb-infected cell line were both cultured in hollow-fiber bioreactors under conditions as described herein above (and in detail in the '202 patent, incorporated supra) that allowed for expression of the construct encoding sHLA-E*01:03, loading of endogenously produced peptide therein, and secretion of the trimolecular complexes from the cells. The supernatant containing the sHLA-E*01:03/peptide trimolecular complexes was then harvested from the hollow-fiber bioreactors, and the uninfected and Mtb-infected harvested supernatants were then treated in an identical manner post-removal from the hollow-fiber bioreactors.

Trimolecular sHLA-E*01:03/peptide complexes were affinity purified from the uninfected and Mtb-infected supernatants using an anti-HLA antibody (such as, but not limited to, W6/32). Following elution, peptides were isolated from the sHLA-E*01:03 molecules and separated by reverse phase HPLC fractionation. Separate but identical peptide purifications (including the same buffer preparations) were performed for each peptide-batch from both uninfected and infected cells.

Fractionated peptides were then mapped by mass spectrometry to generate fraction-based ion maps. The MS ion maps so produced were assessed for the presence of differences in the ions represented by the spectra. Ions corresponding to the following categories were selected for MS/MS sequencing: (1) upregulation in Mtb-infected cells (at least 1.5-fold over the same ion in uninfected cells), (2) down regulation in Mtb-infected cells (at least 1.5-fold over the same ion in the uninfected cells), (3) presence of the ion only in Mtb-infected cells, or (4) absence of ion in Mtb-infected cells that is present in uninfected cells. In addition, multiple parameters were established before peptides were assigned to one of the above categories, including checking the peptide fractions preceding and following the peptide fraction by MS/MS (to ensure that the peptide of interest was not present in an earlier or later fraction) as well as generation of synthetic peptides and subjection to MS/MS to check for an exact match.

Table I lists peptide ligands that have been identified as being presented by the HLA-E*01:03 molecule on the Mtb-infected cell line but not on the uninfected cell line, or presented in a substantially greater amount on the Mtb-infected cell line when compared to the uninfected cell line. One of ordinary skill in the art can appreciate the novelty and usefulness of these peptide ligands and the importance such identification has for numerous therapeutic (i.e., vaccine development, drug targeting, and the like) and diagnostic tools.

The sequences in Table I represent single-letter abbreviations of amino acids within a peptide. A peptide is defined as a short polymer of amino acids. The order of these amino acids is written from N-terminal end of the peptide to the C-terminal end of the peptide.

The presently disclosed or claimed inventive concept(s) includes improved methodology for ligand screening titled Deep Ligand Sequencing (DLS), performed with a combination of next-generation, high sensitivity, high mass accurate quadruple time of flight (QTOF; TOFTRIPLETOF® 5600+ mass spectrometer (AB Sciex Pte. Ltd., Framingham, Mass.)) with two-dimensional nano-LC/MS. This method is summarized in FIG. 1.

TABLE 1

HLA-E Peptide Epitopes Unique to Mtb-infected Cells

| Peptide SEQ ID NO: | Peptide Sequence | Gene | Source Protein | Source Protein SEQ ID NO: |
|---|---|---|---|---|
| 1 | AERAPVEADAGGGQKVLVRN | epsA | ESX-1 secretion-associated protein A, EspA | 30 |
| 2 | STEGNVTGMFA | esxA | 6 kDa early secretory antigenic target EsxA (ESAT-6) | 31 |
| 3 | STEGNVTGM(/15.99)FA | esxA | 6 kDa early secretory antigenic target EsxA (ESAT-6) | 31 |

TABLE 1-continued

HLA-E Peptide Epitopes Unique to Mtb-infected Cells

| Peptide SEQ ID NO: | Peptide Sequence | Gene | Source Protein | Source Protein SEQ ID NO: |
|---|---|---|---|---|
| 4 | LLDEGKQSL | esxA | 6 kDa early secretory antigenic target EsxA (ESAT-6) | 31 |
| 5 | SLLDEGKQSL | esxA | 6 kDa early secretory antigenic target EsxA (ESAT-6) | 31 |
| 6 | SLLDAHIPQ | esxG | ESAT-6 like protein EsxG | 32 |
| 7 | SLLDAHIPQL | esxG | ESAT-6 like protein EsxG | 32 |
| 8 | LLDAHIPQL | esxG | ESAT-6 like protein EsxG | 32 |
| 9 | LLDAHIPQ | esxG | ESAT-6 like protein EsxG | 32 |
| 10 | TLLDVAQANLGEAAGTYV | esxG | ESAT-6 like protein EsxG | 32 |
| 11 | NLGEAAGTYV | esxG | ESAT-6 like protein EsxG | 32 |
| 12 | IMYNYPAML | esxH | Low molecular weight protein antigen 7 EsxH | 33 |
| 13 | IM(+15.99)YNYPAM(+15.99)L | esxH | Low molecular weight protein antigen 7 EsxH | 33 |
| 14 | PALPPAPPSP | GI:5305335 | Proline-rich muscin homolog | 34 |
| 15 | LPPAPPAPPS | GI:544648605 | Proline-rich muscin-like protein | 35 |
| 16 | GLIDIAPHQISSVAA | iniB | Isoniazid inducible gene protein IniB | 36 |
| 17 | GGILIGSDTDLT | lpql | Probable conserved lipoprotein Lpql | 37 |
| 18 | HVGGILIGSDTDLT | lpql | Probable conserved lipoprotein Lpql | 37 |
| 19 | VGGILIGSDTDLT | lpql | Probable conserved lipoprotein Lpql | 37 |
| 20 | AEIVAGGGPLPL | lpql | Probable conserved lipoprotein Lpql | 37 |
| 21 | PAILRPGRLD | mpa | Mycobacterial proteasome ATPase Mpa | 38 |
| 22 | RVVPEGLAAA | PE5 | PE family protein PE5 | 39 |
| 23 | ADVVGSDDLIE | rplA | 50S ribosomal protein L1 RplA | 40 |
| 24 | AGADVVGSDDLIE | rplA | 50S ribosomal protein L1 RplA | 40 |
| 25 | ATNRPDLID | Rv0435c/ftsH | Putative conserved ATPase/Membrane-bound protease FtsH | 41 |
| 26 | TNRPDLID | Rv0435c/ftsH | Putative conserved ATPase/Membrane-bound protease FtsH | 41 |
| 27 | EIEVDDDLIQK | Rv0634A | Hypothetical protein | 42 |
| 28 | S(+42.01)TIIAGALLLVL | Rv3479 | Possible transmembrane protein | 43 |
| 29 | LIGPPPSP | Rv3491 | Hypothetical protein | 44 |

+15.99 refers to an oxidized methionine; +42.01 refers to an N-terminal acetylation Directly eluted HLA peptides are very complex and contain a mixture of tens of thousands of biochemically similar peptides of comparable mass. Thus, multiple dimensions of biochemical separation are needed for comparative analysis of individual peptide ligands. Fortunately, modern mass spectrometers are equipped with two-dimensional HPLC that precedes mass spectrometric separation by mass and charge; thus, multiple dimensions of candidate epitope separation are incorporated into the latest equipment. Here, a two-dimensional LC-MS approach followed by MS1 and MS2 enabled efficient separation and sequencing of directly eluted ligands (FIG. 1). A precise assignment of mass eliminated false positive hits in the MASCOT™ (Matrix Science, Boston, Mass.), PEAKS® (Bioinformatic Solutions Inc., Waterloo, ON, Canada), and ProteinPilot™ (AB Sciex Pte. Ltd., Framingham, Mass.) algorithms. The TRIPLETOF® 5600+ mass spectrometer (AB Sciex Pte. Ltd., Framingham, Mass.) has been applied herein for accurate and sensitive identification of ligand sequences from MS2 fragment spectra. Using this deep ligand sequencing method, it was possible to reach T-cell sensitivities while still allowing for the de novo identification of greater than 10,000 high-confidence ligand sequences.

For the first dimension, the directly eluted peptide pool was loaded on a reverse phase JUPITER® 4 μm Proteo 90 Å, 2 mm id×150 mm long column (Phenomonex, Inc., Torrance, Calif.) with a Paradigm MG4 HPLC (Michrom Biosciences Inc., Auburn, Calif.). Peptides were eluted from the column in high pH conditions (pH 10) with a gradient of 2-10% acetonitrile in water in 2 minutes, then 10-60% in 60 minutes. Forty peptide-rich fractions were collected along the gradient. All 40 fractions from the first-dimension were dried by vacuum centrifugation. Each fraction was solubilized in a 1:1 second dimension solvent A/dimethylformamide and placed into the 96-well high-throughput autosampler of an Eksigent NanoLC 400 U-HPLC system (AB Sciex Pte. Ltd., Framingham, Mass.). One-tenth of each sample was sequentially run in triplicate on a reversed-phase nano-HPLC column equilibrated at pH 2. The second-dimension nano-HPLC setup included a 350 micron id×0.5 mm long ChromXP C18 trap column (AB Sciex Pte. Ltd., Framingham, Mass.) with 3 micron particles and 120 Angstrom pores and a ChromXP C18 separation column (AB Sciex Pte. Ltd., Framingham, Mass.) of dimensions 75 micron id×15 cm length packed with the same media. The solvent system was comprised of two solvents, A and B; solvent A contained 0.1% formic acid in 98% water and 2% acetonitrile, while solvent B contained 0.1% formic acid in 5% water and 95% acetonitrile. Samples were loaded on the trap column at a flow rate of 10 μl/minute.

Next, the trap column was placed in-line with the separation column running at a flow rate of 300 nL/minute. Peptides were then eluted utilizing a program with two linear gradients. The bulk of the peptides were eluted in the initial gradient of 5% to 40% solvent B over 70 minutes. Any remaining peptides were eluted in the second gradient of 40% to 80% solvent B over ten minutes. The second-dimension HPLC column effluent was connected to the nanospray III ion source of a quadrupole-TOF mass spectrometer (TRIPLETOF® 5600+ mass spectrometer (AB Sciex Pte. Ltd., Framingham, Mass.)) to generate LC/MS ion maps and parent ion MS/MS fragmentation spectra.

Forty second dimension LC/MS1 spectra were comparatively analyzed, and candidate ligand sequences from Mtb-infected cells were identified (FIG. 1). Briefly, corresponding LC/MS1 spectra from each fraction were aligned; after alignment, corresponding LC/MS1 ion maps from Mtb-infected and uninfected cells were compared using MarkerView™ software (AB Sciex Pte. Ltd., Framingham, Mass.). Unique ions corresponding to the Mtb cell line fraction were identified, placed on an inclusion list for Information Dependant Acquisition (AB Sciex Pte. Ltd., Framingham, Mass.), and subjected to LC/MS2 fragmentation (if not completed in the first round of MS acquisition) in order to identify amino acid sequences.

MS2 fragment spectra for directly eluted HLA peptides can be challenging to interpret, because HLA-presented peptides are not tryptic peptides: the C-terminus thereof often lacks a charge. Because of the unique nature of HLA peptides, a multi-layered complementary approach was taken to resolve MS2 fragmentation data, utilizing a combined application of the current algorithms MASCOT™ (Matrix Science, Boston, Mass.), PEAKS® (Bioinformatic Solutions Inc., Waterloo, ON, Canada), and ProteinPilot™ (AB Sciex Pte. Ltd., Framingham, Mass.). Using this approach, over 10,000 peptides were sequenced with high confidence, including any peptides that were post-translationally modified (which includes approximately greater than 20% of the ligands). To avoid false positive sequences, the corresponding synthetic peptide of any assigned sequence was generated and subjected to the same LC/MS/MS method. The assigned sequence would only be considered correct when the MS/MS spectra and LC retention time from the synthetic peptide matched the native peptide.

Thus, in accordance with the presently disclosed and/or claimed inventive concept(s), there has been provided compositions that include HLA-E binding epitopes identified by a method of epitope discovery, comparative ligand mapping, and deep ligand sequencing, as well as compositions including same and methods of identification, production, and use thereof, that fully satisfy the objectives and advantages set forth herein above. Although the inventive concept(s) has been described in conjunction with the specific drawings, experimentation, results and language set forth herein above, it is evident that many alternatives, modifications, and variations will be apparent to those of ordinary skill in the art. Accordingly, it is intended to embrace all such alternatives, modifications, and variations that fall within the spirit and broad scope of the inventive concept(s).

What is claimed is:

1. A composition, comprising at least one of:
   (a) an isolated class I HLA trimolecular complex formed in vitro, the trimolecular complex comprising a soluble, truncated HLA-E heavy chain, beta-2-microglobulin, and a peptide consisting of SEQ ID NO:1, and wherein the soluble, truncated HLA-E heavy chain does not contain the transmembrane and cytoplasmic domains of the native, full length HLA-E heavy chain;
   (b) an isolated class I HLA trimolecular complex formed in vitro, the trimolecular complex comprising a soluble, truncated HLA-E heavy chain, beta-2-microglobulin, and a peptide consisting of SEQ ID NO:2 or 3, and wherein the soluble, truncated HLA-E heavy chain does not contain the transmembrane and cytoplasmic domains of the native, full length HLA-E heavy chain;
   (c) an isolated class I HLA trimolecular complex formed in vitro, the trimolecular complex comprising a soluble, truncated HLA-E heavy chain, beta-2-microglobulin, and a peptide consisting of SEQ ID NO:4, and wherein the soluble, truncated HLA-E heavy chain does not contain the transmembrane and cytoplasmic domains of the native, full length HLA-E heavy chain;
   (d) an isolated class I HLA trimolecular complex formed in vitro, the trimolecular complex comprising a soluble, truncated HLA-E heavy chain, beta-2-microglobulin, and a peptide consisting of SEQ ID NO:5, and wherein the soluble, truncated HLA-E heavy chain does not contain the transmembrane and cytoplasmic domains of the native, full length HLA-E heavy chain;
   (e) an isolated class I HLA trimolecular complex formed in vitro, the trimolecular complex comprising a soluble, truncated HLA-E heavy chain, beta-2-microglobulin, and a peptide consisting of one of SEQ ID NOS:6-9, and wherein the soluble, truncated HLA-E heavy chain does not contain the transmembrane and cytoplasmic domains of the native, full length HLA-E heavy chain;
(f) an isolated class I HLA trimolecular complex formed in vitro, the trimolecular complex comprising a soluble, truncated HLA-E heavy chain, beta-2-microglobulin, and a peptide consisting of SEQ ID NO:10 or 11, and wherein the soluble, truncated HLA-E heavy chain does not contain the transmembrane and cytoplasmic domains of the native, full length HLA-E heavy chain;
(g) an isolated class I HLA trimolecular complex formed in vitro, the trimolecular complex comprising a soluble, truncated HLA-E heavy chain, beta-2-microglobulin, and a peptide consisting of SEQ ID NO:12 or 13, and wherein the soluble, truncated HLA-E heavy chain does not contain the transmembrane and cytoplasmic domains of the native, full length HLA-E heavy chain;
(h) an isolated class I HLA trimolecular complex formed in vitro, the trimolecular complex comprising a soluble, truncated HLA-E heavy chain, beta-2-microglobulin, and a peptide consisting of SEQ ID NO:14, and wherein the soluble, truncated HLA-E heavy chain does not contain the transmembrane and cytoplasmic domains of the native, full length HLA-E heavy chain;
(i) an isolated class I HLA trimolecular complex formed in vitro, the trimolecular complex comprising a soluble, truncated HLA-E heavy chain, beta-2-microglobulin, and a peptide consisting of SEQ ID NO:15, and wherein the soluble, truncated HLA-E heavy chain does not contain the transmembrane and cytoplasmic domains of the native, full length HLA-E heavy chain;
(j) an isolated class I HLA trimolecular complex formed in vitro, the trimolecular complex comprising a soluble, truncated HLA-E heavy chain, beta-2-microglobulin, and a peptide consisting of SEQ ID NO:16, and wherein the soluble, truncated HLA-E heavy chain does not contain the transmembrane and cytoplasmic domains of the native, full length HLA-E heavy chain;
(k) an isolated class I HLA trimolecular complex formed in vitro, the trimolecular complex comprising a soluble, truncated HLA-E heavy chain, beta-2-microglobulin, and a peptide consisting of one of SEQ ID NOS:17-20, and wherein the soluble, truncated HLA-E heavy chain does not contain the transmembrane and cytoplasmic domains of the native, full length HLA-E heavy chain;
(l) an isolated class I HLA trimolecular complex formed in vitro, the trimolecular complex comprising a soluble, truncated HLA-E heavy chain, beta-2-microglobulin, and a peptide consisting of SEQ ID NO:21, and wherein the soluble, truncated HLA-E heavy chain does not contain the transmembrane and cytoplasmic domains of the native, full length HLA-E heavy chain;
(m) an isolated class I HLA trimolecular complex formed in vitro, the trimolecular complex comprising a soluble, truncated HLA-E heavy chain, beta-2-microglobulin, and a peptide consisting of SEQ ID NO:22, and wherein the soluble, truncated HLA-E heavy chain does not contain the transmembrane and cytoplasmic domains of the native, full length HLA-E heavy chain;
(n) an isolated class I HLA trimolecular complex formed in vitro, the trimolecular complex comprising a soluble, truncated HLA-E heavy chain, beta-2-microglobulin, and a peptide consisting of SEQ ID NO:23 or 24, and wherein the soluble, truncated HLA-E heavy chain does not contain the transmembrane and cytoplasmic domains of the native, full length HLA-E heavy chain;
(o) an isolated class I HLA trimolecular complex formed in vitro, the trimolecular complex comprising a soluble, truncated HLA-E heavy chain, beta-2-microglobulin, and a peptide consisting of SEQ ID NO:25 or 26, and wherein the soluble, truncated HLA-E heavy chain does not contain the transmembrane and cytoplasmic domains of the native, full length HLA-E heavy chain;
(p) an isolated class I HLA trimolecular complex formed in vitro, the trimolecular complex comprising a soluble, truncated HLA-E heavy chain, beta-2-microglobulin, and a peptide consisting of SEQ ID NO:27, and wherein the soluble, truncated HLA-E heavy chain does not contain the transmembrane and cytoplasmic domains of the native, full length HLA-E heavy chain;
(q) an isolated class I HLA trimolecular complex formed in vitro, the trimolecular complex comprising a soluble, truncated HLA-E heavy chain, beta-2-microglobulin, and a peptide consisting of SEQ ID NO:28, and wherein the soluble, truncated HLA-E heavy chain does not contain the transmembrane and cytoplasmic domains of the native, full length HLA-E heavy chain; and
(r) an isolated class I HLA trimolecular complex formed in vitro, the trimolecular complex comprising a soluble, truncated HLA-E heavy chain, beta-2-microglobulin, and a peptide consisting of SEQ ID NO:29, and wherein the soluble, truncated HLA-E heavy chain does not contain the transmembrane and cytoplasmic domains of the native, full length HLA-E heavy chain.

2. The composition of claim 1, wherein the HLA-E of (a)-(r) is HLA-E*01:01 or HLA-E*01:03.

3. The composition of claim 1, wherein the HLA-E heavy chain of one of (a)-(r) is further defined as a soluble, recombinantly produced HLA-E heavy chain.

4. The composition of claim 3, wherein the class I HLA trimolecular complex of one of (a)-(r) is produced in a host cell made recombinant by a construct encoding the soluble, truncated HLA-E heavy chain, and wherein the construct does not encode the transmembrane and cytoplasmic domains of the native, full length HLA-E heavy chain, and wherein the peptide is further defined as an endogenous peptide that is produced by the host cell and loaded in the trimolecular complex by the host cell.

5. The composition of claim 1, wherein the peptide of one of (a)-(r) is a synthetic peptide.

6. The composition of claim 1, wherein the peptide of one of (a)-(r) is further defined as a peptide having a length of from 8 to 20 amino acids.

\* \* \* \* \*

UNITED STATES PATENT AND TRADEMARK OFFICE
CERTIFICATE OF CORRECTION

PATENT NO. : 10,857,219 B2
APPLICATION NO. : 14/671322
DATED : December 8, 2020
INVENTOR(S) : Hildebrand et al.

It is certified that error appears in the above-identified patent and that said Letters Patent is hereby corrected as shown below:

On the Title Page

In Column 2, item (56), Other Publications, Line 5, delete "( J." and insert -- (J. --.

In Column 2, item (56), Other Publications, Line 15, delete "Moitifs" and insert -- Motifs --.

In Column 2, item (57), Abstract, Line 1, after "include" insert -- at least --.

On page 2, in Column 1, item (56), Other Publications, Line 23, delete "Electrspray" and insert -- Electrospray --.

On page 2, in Column 1, item (56), Other Publications, Line 27, delete "motiff" and insert -- motif --.

On page 2, in Column 1, item (56), Other Publications, Line 34, delete "articiial" and insert -- artificial --.

On page 2, in Column 1, item (56), Other Publications, Line 44, delete "Spectrometic" and insert -- Spectrometric --.

On page 2, in Column 1, item (56), Other Publications, Line 55, delete "memebrane" and insert -- membrane --.

On page 2, in Column 2, item (56), Other Publications, Lines 5-6, delete "HIstocompatibility" and insert -- Histocompatibility --.

On page 2, in Column 2, item (56), Other Publications, Line 20, delete "interations" and insert -- interactions --.

On page 2, in Column 2, item (56), Other Publications, Line 26, delete "Peptid-Specific," and insert -- Peptide-Specific, --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,857,219 B2

On page 3, in Column 1, item (56), Other Publications, Line 16, delete ":Allele-specifric" and insert -- :Allele-specific --.

On page 3, in Column 1, item (56), Other Publications, Line 17, delete "molecues," and insert -- molecules, --.

On page 3, in Column 1, item (56), Other Publications, Line 29, delete "Histocompatibiltiy" and insert -- Histocompatibility --.

On page 3, in Column 2, item (56), Other Publications, Line 7, delete ""Identifiation" and insert -- "Identification --.

On page 3, in Column 2, item (56), Other Publications, Line 8, delete "oby" and insert -- by --.

On page 3, in Column 2, item (56), Other Publications, Line 12, delete "Suptertype,"" and insert -- Supertype," --.

On page 3, in Column 2, item (56), Other Publications, Line 14, delete "interations" and insert -- interactions --.

On page 3, in Column 2, item (56), Other Publications, Line 35, delete "Histocompatibilty" and insert -- Histocompatibility --.

On page 3, in Column 2, item (56), Other Publications, Line 35, delete "Immunoreative" and insert -- Immunoreactive --.

On page 3, in Column 2, item (56), Other Publications, Line 40, delete "lmmunolgoy," and insert -- Immunology, --.

On page 3, in Column 2, item (56), Other Publications, Line 58, delete "produciton" and insert -- production --.

On page 3, in Column 2, item (56), Other Publications, Line 59, delete "Immunogentics," and insert -- Immunogenetics, --.

In the Specification

In Column 4, Line 7, delete "(2nd" and insert -- 2nd --.

In Column 6, Line 2, delete "supercede" and insert -- supersede --.

In Column 14, Line 42, delete "or" and insert -- and/or --.

In Column 14, Line 46, delete "TOFTRIPLETOF" and insert -- TRIPLETOF --.

CERTIFICATE OF CORRECTION (continued)
U.S. Pat. No. 10,857,219 B2

In Columns 13 and 14, Table 1, Peptide SEQ ID NO: 3, Line 1, delete "(/15.99) FA" and insert -- (+15.99) FA --.

In Columns 15 and 16, Table 1-continued, Peptide SEQ ID NO: 14, Line 1, delete "muscin" and insert -- mucin --.

In Columns 15 and 16, Table 1-continued, Peptide SEQ ID NO: 15, Line 1, delete "muscin-like" and insert -- mucin-like --.

In Columns 15 and 16, Table 1-continued, Peptide SEQ ID NO: 16, Line 1, delete "inductible" and insert -- inducible --.

In Column 17, Line 26, delete "(Phenomonex," and insert -- (Phenomenex, --.

In Column 18, Lines 17-18, delete "Dependant" and insert -- Dependent --.

In the Claims

In Column 60, Line 43, Claim 3, after "chain of" insert -- at least --.

In Column 60, Line 46, Claim 4, after "complex of" insert -- at least --.

In Column 60, Line 54, Claim 5, after "peptide of" insert -- at least --.

In Column 60, Line 56, Claim 6, after "peptide of" insert -- at least --.